United States Patent
El-Khouri et al.

(10) Patent No.: US 10,369,387 B2
(45) Date of Patent: *Aug. 6, 2019

(54) COSMETIC COMPOSITIONS CAPABLE OF FORMING A MULTILAYER STRUCTURE AFTER APPLICATION TO A KERATINOUS MATERIAL

(71) Applicant: L'ORÉAL, Paris (FR)

(72) Inventors: Rita Jaky El-Khouri, Morristown, NJ (US); Jody Ebanks, Bloomfield, NJ (US); Rabia Ahmad, Queens, NY (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/445,634

(22) Filed: Feb. 28, 2017

(65) Prior Publication Data

US 2018/0243201 A1 Aug. 30, 2018

(51) Int. Cl.
*A61K 8/893* (2006.01)
*A61K 8/891* (2006.01)
*A61K 8/31* (2006.01)
*A61Q 1/02* (2006.01)
*A61K 8/892* (2006.01)

(52) U.S. Cl.
CPC ............... *A61Q 1/02* (2013.01); *A61K 8/31* (2013.01); *A61K 8/891* (2013.01); *A61K 8/893* (2013.01); *A61K 2800/31* (2013.01); *A61K 2800/882* (2013.01)

(58) Field of Classification Search
None
See application file for complete search history.

(56) References Cited

U.S. PATENT DOCUMENTS

| | | |
|---|---|---|
| 4,767,741 A | 8/1988 | Komor et al. |
| 5,849,316 A | 12/1998 | Mullul et al. |
| 5,882,635 A | 3/1999 | Ramin et al. |
| 5,985,297 A | 11/1999 | Mullul et al. |
| 6,019,962 A | 2/2000 | Rabe et al. |
| 6,071,503 A | 6/2000 | Drechsler et al. |
| 6,340,466 B1 | 1/2002 | Drechsler et al. |
| 6,406,683 B1 | 6/2002 | Drechsler et al. |
| 6,482,398 B1 | 11/2002 | Rabe et al. |
| 6,620,417 B1 | 9/2003 | Jose et al. |
| 6,811,770 B2 | 11/2004 | Ferrari et al. |
| 7,094,944 B2 * | 8/2006 | Faasse, Jr. .......... A61F 13/0259 602/42 |
| 7,785,574 B2 | 8/2010 | Bobka et al. |
| 8,277,791 B2 | 10/2012 | Zheng et al. |
| 9,205,039 B2 | 12/2015 | Brown et al. |
| 2001/0031269 A1 | 10/2001 | Arnaud |
| 2003/0068344 A1 | 4/2003 | Ferrari et al. |
| 2005/0089498 A1 | 4/2005 | Patil et al. |
| 2005/0186166 A1 | 8/2005 | Patil et al. |
| 2005/0201961 A1 | 9/2005 | Lu et al. |
| 2005/0226832 A1 | 10/2005 | Bobka et al. |
| 2005/0244355 A1 | 11/2005 | Sabino et al. |
| 2005/0249758 A1 | 11/2005 | Di Puccio Pagano |
| 2006/0292096 A1 | 12/2006 | Yu |
| 2007/0093619 A1 | 4/2007 | Bui et al. |
| 2008/0305056 A1 | 12/2008 | Klaus et al. |
| 2008/0305068 A1 | 12/2008 | Zheng et al. |
| 2011/0147259 A1 | 6/2011 | Binder et al. |
| 2012/0276034 A1 | 11/2012 | Zheng et al. |
| 2013/0164229 A1 | 6/2013 | Mendoza |
| 2014/0154196 A1 | 6/2014 | Cavazzuti et al. |
| 2014/0154199 A1 | 6/2014 | Dussaud et al. |
| 2015/0366779 A1 | 12/2015 | Bui et al. |
| 2015/0366780 A1 * | 12/2015 | Bui .................. A61K 8/895 424/64 |
| 2015/0366782 A1 | 12/2015 | Bui et al. |

(Continued)

FOREIGN PATENT DOCUMENTS

WO  WO 2014/095821 A1  6/2014
WO  WO 2015/193413 A1  12/2015

OTHER PUBLICATIONS

Factsheet: Dow Corning 670 Fluid—Intellectual Property (2005, pp. 1-7) (Year: 2005).*
KP-550 Technical Data Sheet, Shin-Etsu, 2012, pp. 1-2 (Year: 2012).*
U.S. Appl. No. 15/144,698, filed May 2, 2016, US 2017-0281518 A1 Oct. 2017, Rita Jaky El-Khouri.
U.S. Appl. No. 15/144,622, filed May 2, 2016, US 2017-0281478 A1 Oct. 2017, Rita Jaky El-Khouri.
U.S. Appl. No. 15/144,716, filed May 2, 2016, US 2017-0281518 A1 Oct. 2017, Rita Jaky El-Khouri.

(Continued)

*Primary Examiner* — Ernst V Arnold
*Assistant Examiner* — Kyung S Chang
(74) *Attorney, Agent, or Firm* — Oblon, McClelland, Maier & Neustadt, L.L.P.

(57) ABSTRACT

Cosmetic compositions (e.g., foundation, primer, eye shadow or other skin composition) capable of forming a multilayer structure after application to a keratinous material are provided, as well as methods of using same. Certain compositions comprise at least two immiscible components: Component A which comprises about 0.01% to 60% by weight with respect to the total weight of the composition of at least one silicone- and/or hydrocarbon-containing film forming agent having at least one glass transition temperature lower than normal human body temperature; and Component B which comprises about 0.01% to 90% by weight with respect to the total weight of the composition of one or more silicone compounds in amounts sufficient to achieve a viscosity of about 1,000 cSt to 2,000,000 cSt, wherein the weight ratio of the silicone- and/or hydrocarbon-containing film forming agent(s) in Component A to silicone compound(s) in Component B is from about 1:50 to 1.5:1.

20 Claims, No Drawings

(56) References Cited

U.S. PATENT DOCUMENTS

2016/0228349 A1   8/2016   Dussaud et al.

OTHER PUBLICATIONS

U.S. Appl. No. 15/253,071, filed Aug. 31, 2016, US 2017-0281518 A1 Oct. 2017, Rita Jaky El-Khouri.
U.S. Appl. No. 15/253,114, filed Aug. 31, 2016, Rita Jaky El-Khouri.
U.S. Appl. No. 15/857,045, filed Dec. 28, 2017, Rita Jaky El-Khouri.
U.S. Appl. No. 15/719,788, filed Sep. 29, 2017, Rita Jaky El-Khouri.
U.S. Appl. No. 15/720,341, filed Sep. 29, 2017, Rita Jaky El-Khouri.
U.S. Appl. No. 15/857,066, filed Dec. 28, 2017, Rita Jaky El-Khouri.
The International Search Report and Written Opinion of the International Searching Authority dated Jul. 11, 2017 in PCT/US2017/025376 filed Mar. 31, 2017, 14 pages.
"Xiameter(R) PMX-200 Silicone Fluid 30,000 CS" XIAMETER® from Dow Corning, Safety Data Sheet, Version 3.0, Revision Date: Sep. 13, 2017, pp. 1-12.
"XIAMETER® PMX-200 Silicone Fluid, 5,000-60,000 cSt" XIAMETER® from Dow Corning, Feb. 18, 2015, 3 Pages.
"Mega Last Liquid Lipstick, Liquid Lipstick: Improved Color Intensity, Non-transfer" Formulation 01451, Dow Corning®, Formulation Information, Color Cosmetics, 2010, 2 Pages.
Alex C. M. Kuo, "Poly(dimethylsiloxane)" Polymer Data Handbook, Copyright © by Oxford University Press, Inc., 1999, pp. 411-435.
"Introduction to Silicone Fluids" Clearco, Aug. 7, 2006, 4 Pages.
Triethoxy Caprylylsilane Treatment—11S KOBO, Jul. 14, 2017, 2 pages.

* cited by examiner

COSMETIC COMPOSITIONS CAPABLE OF FORMING A MULTILAYER STRUCTURE AFTER APPLICATION TO A KERATINOUS MATERIAL

FIELD OF THE INVENTION

The present invention relates to cosmetic compositions capable of forming a multilayer structure after application to a keratinous material. Such compositions allow for benefits associated with multilayer cosmetic products without having to engage in a multi-step application process.

DISCUSSION OF THE BACKGROUND

Many cosmetic compositions, including pigmented cosmetics such as foundations and eye shadows, have been formulated in an attempt to possess long wearing properties upon application. Unfortunately, many of these compositions do not generally possess both good long-wear/transfer-resistance properties as well as good application properties, good comfort properties and/or good appearance properties (for example, shine, or matte properties).

For example, with respect to foundations, such products can provide good long wear properties and/or transfer-resistance. However, such long-wearing/transfer-resistant products can possess poor application and/or feel upon properties application, as well as poor matte properties.

Thus, there remains a need for improved "single step" cosmetic compositions having improved cosmetic properties, particularly good wear, feel, radiance, luminosity, and/or matte characteristics upon application.

SUMMARY OF THE INVENTION

The present invention relates to cosmetic compositions capable of forming a multilayer structure after application to a keratinous material.

Accordingly, one aspect of the present invention relates to a cosmetic composition capable of forming a multilayer structure after application to skin, wherein the cosmetic composition comprises at least two immiscible components. Component A comprises about 0.01% to 60% by weight with respect to the total weight of the composition of at least one silicone- and/or hydrocarbon-containing film forming agent having at least one glass transition temperature which is lower than normal human body temperature, Component B comprises about 0.01% to 90% by weight with respect to the total weight of the composition of one or more silicone compounds in amounts sufficient to achieve a viscosity of about 1,000 cSt to 22,000,000 cSt. The weight ratio of the silicone- and/or hydrocarbon-containing film forming agent(s) in Component A to silicone compound(s) in Component B may be from about 1:50 to 1.5:1.

In one or more embodiments, the cosmetic composition comprises at least two immiscible components prior to application. In some embodiments, the cosmetic composition further comprises a pigment. In one or more embodiments, the pigment is an inorganic pigment. In some embodiments, the inorganic pigment is selected from the group consisting of iron oxide, titanium oxide, ultramarine blue and combinations thereof. In one or more embodiments, the cosmetic composition further comprises a mattifying agent selected from the group consisting of a talc, silica, silicone elastomer, polyamide, wax, and combinations thereof. In some embodiments, the cosmetic composition is anhydrous. In one or more embodiments, Component A comprises at least one silicone-containing film forming agent having at least one glass transition temperature lower than 60° C. In some embodiments, the cosmetic composition further comprises a skin active agent, skin adjuvant, or UV filter. In one or more embodiments, the silicone compound comprises at least one polymer selected from the group consisting of a silicone gum, a silicone fluid, and mixtures thereof. In some embodiments, the at least one silicone- and/or hydrocarbon-containing film forming agent comprises a hydrocarbon-containing film forming agent selected from the group consisting of polysaccharides, high viscosity esters, polybutenes, polyisobutenes, polyhydrogenated butenes, acrylic polymers, acrylate copolymers, vinyl pyrrolidone (VP) containing homopolymers and copolymers, polyurethanes, polyolefins and mixtures thereof. In one or more embodiments, the at least one at least one silicone- and/or hydrocarbon-containing film forming agent comprises at least one film forming agent selected from the group consisting of a silicone resin, a silicone acrylate copolymer, and mixtures thereof.

Another aspect of the invention pertains to a kit comprising: (a) the cosmetic composition according to claim 1; (b) at least one container which contains any of the cosmetic composition described herein; and (c) at least one applicator. In some embodiments, the at least one container is configured to mix Components A and B.

Another aspect of the invention pertains to a method of applying the cosmetic compositions described herein. In one or more embodiments, the method comprises mixing the cosmetic composition to form a mixed composition in which Component A and Component B are temporarily miscible, and applying the mixed composition to the keratinous material. In one or more embodiments, the keratinous material comprises skin. In some embodiments, the silicone compound comprises at least one polymer selected from the group consisting of a silicone gum, a silicone fluid, and mixtures thereof. In one or more embodiments, the at least one silicone- and/or hydrocarbon-containing film forming agent comprises a hydrocarbon-containing film forming agent selected from the group consisting of polysaccharides, high viscosity esters, polybutenes, polyisobutenes, polyhydrogenated butenes, acrylic polymers, acrylate copolymers, vinyl pyrrolidone (VP) containing homopolymers and copolymers, polyurethanes, polyolefins and mixtures thereof. In some embodiments, the at least one at least one silicone- and/or hydrocarbon-containing film forming agent comprises at least one film forming agent selected from the group consisting of a silicone resin, a silicone acrylate copolymer, and mixtures thereof. In one or more embodiments, the composition further comprises a pigment.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Film former" or "film forming agent" as used herein means a polymer or resin that leaves a film on the substrate to which it is applied.

"Polymer" as used herein means a compound which is made up of at least two monomers.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, hydroxyalkyl groups, and polysiloxane groups. The substituent(s) may be further substituted.

"Volatile", as used herein, means having a flash point of less than about 100° C.

"Non-volatile", as used herein, means having a flash point of greater than about 100° C.

"Anhydrous" means the compositions contain less than 1% water. Preferably, the compositions of the present invention contain less than 0.5% water, and most preferably no water.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to human keratin material such as hair, skin or lips followed by rubbing a material, for example, a sheet of paper, against the hair, skin or lips after expiration of a certain amount of time following application, such as 2, 3, 4, 5, 6, 7, 8, 9, 10, 11, 12, 13, 14 or 15 minutes after application. Similarly, transfer resistance of a composition may be evaluated by the amount of product transferred from a wearer to any other substrate, such as transfer from the hair, skin or lips of an individual to a collar when putting on clothing after the expiration of a certain amount of time following application of the composition to the hair, skin or lips. The amount of composition transferred to the substrate (e.g., collar, or paper) may then be evaluated and compared. For example, a composition may be transfer resistant if a majority of the product is left on the wearer's hair, skin or lips. Further, the amount transferred may be compared with that transferred by other compositions, such as commercially available compositions. In a preferred embodiment of the present invention, little or no composition is transferred to the substrate from the hair, skin or lips.

"Adhesion" as used herein refers to the quality exhibited by compositions that adhere to a substrate after application. Adhesion may be evaluated by any method known in the art for evaluating such. For example, samples to be tested for adhesion properties can be deposited onto a surface such as a bioskin substrate or Byko-Charts Black Scrub Panels P122-10N (6.50×17.00 inches). After drying, a piece of ASTM cross hatch tape (Permacel 99/PA-28060/51596) can be placed on the sample, and removed at a 180° angle. Then, it can be determined how much of the sample is adhered to the tape. For example, a rating scale such as a scale of 1-3 can be used to assess the degree of sample removal from the substrate onto the tape, in which 1 is essentially no removal, 2 is some removal, and 3 is essentially complete removal.

The term rub-off resistance as used herein refers to physical abrasion such as rubbing the human skin with the hands or clothes or other physical interaction. It can also be described as the ability to hold active ingredients on the skin or prevent the removal of active ingredients from the skin or a substrate such as Byko-Charts Black Scrub Panels P122-10N (6.50×17.00 inches) or bioskin by abrasion or other physical interaction.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to the skin and evaluating the color of the composition after an extended period of time. For example, the color of a composition may be evaluated immediately following application to skin and these characteristics may then be re-evaluated and compared after a certain amount of time. Further, these characteristics may be evaluated with respect to other compositions, such as commercially available compositions. Alternatively or additionally, long wear properties may be evaluated by applying a sample, allowing it to dry, and then abrading the sample to determine removal/loss of sample.

The cosmetic compositions and methods of the present invention can comprise, consist of, or consist essentially of the essential elements and limitations of the invention described herein, as well as any additional or optional ingredients, components, or limitations described herein or otherwise useful in personal care.

Compositions Capable of Forming a Multilayer Structure

In accordance with various embodiments of the present invention, cosmetic compositions capable of forming a multilayer structure after application to a keratinous material are provided. Such compositions allow for benefits associated with multilayer cosmetic products without having to engage in a multi-step application process. In one or more embodiments, such compositions are suitable as foundations, primers, eye shadows and other skin compositions.

In accordance with one or more embodiments of the present invention, the cosmetic compositions of the present invention comprise at least two Components, hereinafter referred to as "Component A" and "Component B." In one or more embodiments, both Component A and Component B comprise silicone. Component A, for example, may comprise a silicone-containing film-forming agent. Component B, for example, may comprise a silicone gum. In some embodiments, Component A comprises a hydrocarbon film forming agent, and Component B comprises a silicone compound. Again, Component B, for example, may comprise a silicone gum. In one or more embodiments, Component A may comprise both a silicone-containing film forming agent as well as a hydrocarbon-containing film forming agent.

Component A is the component of the compositions of the present invention which forms the layer of the multilayer structure which is closest to the keratinous material after application of the composition to the keratinous material. This layer of the multilayer structure is hereinafter referred to as "Layer A." In accordance with preferred embodiments, Component A/Layer A has an affinity for the surface of the keratinous material owing to the surface energy characteristics between the two.

Component B is the component of the compositions of the present invention which forms the layer of the multilayer structure which is farthest away from the keratinous material after application of the composition to the keratinous material. This layer of the multilayer structure is hereinafter referred to as "Layer B." In accordance with preferred embodiments, Component B/Layer B has an affinity for the air interface.

In accordance with the present invention, all weight amounts and ratios set forth herein referring to Component A and Component B refer to amounts of active material (that is, non-volatile material) in these components. Similarly, all weight amounts and ratios set forth herein referring to Layer A and Layer B refer to amounts of active material as Layer A and Layer B are present after evaporation of volatile solvent.

Prior to application to a keratinous material, Component A and Component B are immiscible in the compositions of the present invention. Preferably, immiscibility of the immiscible components results from an incompatibility between the two components when the composition is at rest, incompatibility between the two components after application to a keratinous material, or both.

In one or more embodiments, immiscibility of the immiscible components results from differences such as, for example, differences in viscosity, glass transition temperature, interfacial tension, solubility parameters, density, and/or chemical/structural incompatibility of the components, and/or differences induced by temperature and/or pressure.

For example, immiscibility of the immiscible components when the composition is at rest can result from, for example, chemical/structural incompatibility, differences in the interfacial tension between the components such as, for example, differences in the interfacial tension between the phases within mutually compatible solvent(s), differences in viscosity, differences in the glass transition temperatures of the polymers within each phase and/or differences induced by temperature and/or pressure.

For example, immiscibility of the immiscible components when the composition is being applied can result from, for example, chemical/structural incompatibility, differences in the interfacial tension between the components, differences in density of the components after solvent evaporation, and/or differences induced by temperature and/or pressure.

In one or more embodiments, immediately prior to application and/or during application to a keratinous material, the composition of the present invention is mixed or blended such that Component A and Component B are temporarily miscible upon application of the composition of the present invention to a keratinous material.

After the composition of the present invention has been applied to a keratinous material, Component A separates from Component B. As the composition dries on the keratinous material to which it has been applied, immiscible Component A and Component B form a multilayer structure comprising Layer A and Layer B, respectively, on the keratinous material such as, for example:

| |
|---|
| LAYER B |
| LAYER A |
| KERATINOUS MATERIAL |

According to one or more embodiments of the present invention, after compositions of the present invention have been applied to a keratinous material, Component B results in Layer B which is level: that is, Layer B is planar such that it may have refractive properties to impart shine to the composition. In accordance with these embodiments, Component B has self-leveling properties: it results in a level Layer B after application. The shine of such compositions can be enhanced, if desired, by addition of one or more shine or gloss enhancing agents having high refractive index properties. Alternatively, such compositions can be provided with matte properties by addition of one or more mattifying agents.

According to preferred embodiments of the present invention, after compositions of the present invention have been applied to a keratinous material, Component B results in Layer B which is not-level: that is, Layer B is not planar such that it imparts matte properties to the composition. In accordance with these embodiments, Component B does not have self-leveling properties: it results in a non-level Layer B after application. The matte properties of such compositions can be enhanced, if desired, by addition of one or more mattifying agents. Alternatively, such compositions can be provided with shine/luminosity properties by addition of one or more shine or gloss enhancing agents having high refractive index properties. Another benefit of the compositions is when used as a base layer/primer, the self-leveling nature of the compositions may provide a smoothing surface, thereby reducing imperfections in the skin.

In accordance with the present invention, the multilayer structure comprises Layer A and Layer B. In certain instances, depending on factors such as ingredient ratios, ingredient concentrations, solvent evaporation characteristics, and Tg of polymers, the layers might be intermixed slightly with each other after application to a keratinous material, resulting in Layer A having a larger amount of A and a smaller amount of B greater and/or Layer B having a larger amount of B and a smaller amount of A. Preferably, Layer A comprises 40% or less of Layer B, preferably 30% or less of Layer B, preferably 20% or less of Layer B, preferably 10% or less of Layer B, and preferably 5% or less of Layer B, including all ranges and subranges therebetween. Similarly, preferably, Layer B comprises 40% or less of Layer A, preferably 30% or less of Layer A, preferably 20% or less of Layer A, preferably 10% or less of Layer B, and preferably 5% or less of Layer A, including all ranges and subranges therebetween.

Factors affecting the separation of Component A and Component B after application to a keratinous material can include, for example, those properties discussed above including but not limited to the surface energy of the substrate, the density of each Component, the evaporation properties of the solvent(s), the Tg of the film formers, and/or the viscosity of the film formers.

Although not wishing to be bound by any particular theory, it is believed that Component A has a surface energy properties closer to the surface energy properties of the keratinous material to which it is applied than Component B. For example, the surface energy of skin is estimated to be 36 mN/m. Accordingly, where Component A has a surface energy of about 36 mN/m, it is believed that Component A can migrate to the skin. Component B would preferably have a lower surface energy, making it more likely that it would migrate toward the air interface.

Although not wishing to be bound by any particular theory, it is believed that interfacial tension of. Components A and B affects phase separation (in particular, the rate at which the Components A and B separate after application). It is believed that such phase separation can be affected by differences such as those discussed above such as, for example, differences in temperature of the Components A and B, in the Tg of the Components A and B (the higher the Tg of a component, the longer it will take for phase separation), in the weight fraction of the film formers, and/or in the pressure of the Components A and B.

Such differences will also be discussed further below.

Glass Transition Temperature (Tg)

According to preferred embodiments, Component A and/or Component B comprises at least one silicone- and/or hydrocarbon-containing film forming agent having at least one glass transition temperature lower than 60° C., preferably lower than 55° C., preferably lower than 50° C., and preferably lower than normal human body temperature (98.6° F. or 37° C.). Preferably, Component A and/or Component B comprises at least one silicone- and/or hydrocarbon-containing film forming agent which has all of its glass transition temperature(s) below human body temperature (98.6° F. or 37° C.). A plasticizer can be added to adjust Tg of the film forming agent(s) as is known in the art. According to preferred embodiments, Layer A and Layer B both comprise at least one forming agent having a glass transition temperature of less than 37° C.

A preferred method of determining Tg is to remove all volatile solvent from the Layer, and determining Tg by Differential Scanning calorimetry.

Density

According to preferred embodiments, Component A and Component B have different density properties, and the difference is such that Component A and Component B are immiscible in the compositions of the present invention. Preferably, Component A/Layer A and Component B/Layer B have a density difference of 0.001-1 kg/m$^3$, preferably 0.005-0.8 kg/m$^3$, and preferably 0.01-0.6 kg/m$^3$.

Temperature

According to preferred embodiments, Component A and Component B are affected by temperature, and the effect is such that Component A and Component B are immiscible in the compositions of the present invention at temperatures below 50° C. for a predetermined amount of time as is known in the art unlike emulsions which are considered to be stable under such conditions.

Weight Fraction

According to preferred embodiments, Component A and/or Component B comprises at least one polymer such as, for example a film forming agent having a critical molecular weight of entanglement ($M_c$) such that:

If present in Component A, the at least one polymer has an $M_c$<wMw, where w=weight fraction and Mw=molecular weight of the polymer; and If present in Component B, the at least one polymer has $M_c \le wMw \le 10^8$ g/mol.

Further, according to preferred embodiments, the viscosity of the at least one polymer in Component B is greater than 350 cSt, preferably greater than 500 cSt, preferably greater than 750 cSt, and preferably greater than 1000 cSt, including all ranges and subranges therebetween.

Ingredients

Component A and Component B can differ in various ways based primarily on the different functionalities associated with Layer A and Layer B. For example, where Layer A performs a transfer-resistance or adherence function, ingredients of Component A can be chosen to effect transfer-resistance or adherence. Similarly, where Layer A performs a color-enhancing function, at least one coloring agent can be added to Component A. And, for example, where Layer B performs a or shine-enhancing function and/or and provides a better feel (for example, affords a more comfortable feeling) and/or provides a barrier layer to inhibit color transfer, ingredients of Component B can be chosen to effect gloss, shine, comfort and/or barrier layer properties. However, it should be understood that at the interface of Layer A and Layer B, the interface of Layer A may possess properties more associated with Layer B (for example, shine) while Layer B may possess properties more associated with Layer A (for example, adhesion).

According to preferred embodiments, Component A comprises at least one silicone- and/or hydrocarbon-containing film forming agent, at least one coloring agent, or both, and Layer A provides adhesion, transfer-resistance and/or color properties to the multilayer structure. According to such embodiments, Component B may comprise at least one shine-enhancing agent, at least one comfort agent and/or at least one barrier agent, and Layer B provides shine, comfort and/or a barrier properties to the multilayer structure.

According to preferred embodiments, the compositions of the present invention contain less than 1% wax and/or less than 1% fluorinated compound.

According to preferred embodiments, the compositions of the present invention contain less than 0.5% wax and/or less than 0.5% fluorinated compound.

According to preferred embodiments, the compositions of the present invention contain no wax and/or no fluorinated compound.

According to preferred embodiments, at least one of the same solvent(s) is used in Component A and Component B. Preferably, of total solvent present in each Component, the majority in each Component is the same.

According to preferred embodiments, the weight ratio of Component A to Component B is from 1:50 to 1.5:1, 1:75 to 1.5:1, from 1:50 to 1.5:1, or from 1:20 to 1.5:1, including all ranges and subranges therebetween.

Examples of acceptable ingredients added to Component A and/or Component B are discussed below.

Film Forming Agent (Film Former)

Compositions of the present invention may comprise at least one silicone- and/or hydrocarbon-containing film forming agent. Silicone and hydrocarbon-containing film forming agents are known in the art, and any silicone- and/or hydrocarbon-containing film forming agent may be used. According to preferred embodiments, at least one silicone and/or hydrocarbon-containing film forming agent having at least one glass transition temperature lower than 60° C., preferably lower than 55° C., preferably lower than 50° C., and preferably lower than normal human body temperature (98.6° F.), is included in the composition of the present invention. Preferably, the at least one silicone and/or hydrocarbon-containing film forming agent has all of its glass transition temperature(s) below 60° C., preferably below than 55° C., preferably below 50° C., and preferably below than normal human body temperature (98.6° F.). The Tg property of the at least one silicone and/or hydrocarbon-containing film forming agent can result from various ways known in the art such as, for example, the Tg of the silicone and/or hydrocarbon-containing film forming agent itself, the combination of different film forming agents to achieve a Tg lower than normal human body temperature, or the combination of film forming agent(s) and plasticizer(s) to achieve a Tg lower than normal human body temperature.

Hydrocarbon-Containing Film Forming Agents (Film Former)

Compositions of the present invention may comprise at least one hydrocarbon-containing film forming agent. As used herein, "hydrocarbon-containing film forming agent" refers to a film forming agent comprising at least about 2.5, 5, 10, 20, 30, 40, 50, 60, 70, 80, 90, 95, or 99% hydrocarbon by weight. In further embodiments, the hydrocarbon-containing film forming agent comprises less than about 5 or 1% silicone resins, and in yet further embodiments, no silicone resins.

Hydrocarbon-containing film forming agents are known in the art, and any hydrocarbon-containing film forming agent may be used. According to preferred embodiments, at least one hydrocarbon-containing film forming agent having at least one glass transition temperature lower than 60° C., preferably lower than 55° C., preferably lower than 50° C., and preferably lower than normal human body temperature (98.6° F.), is included in the composition of the present invention. Preferably, the at least one hydrocarbon-containing film forming agent has all of its glass transition temperature(s) below 60° C., preferably below than 55° C., preferably below than 50° C., and preferably below than normal human body temperature (98.6° F.). The Tg property of the at least one hydrocarbon-containing film forming agent can result from various ways known in the art such as, for example, the Tg of the hydrocarbon-containing film forming agent itself, the combination of different film forming agents to achieve a Tg lower than normal human body temperature, or the combination of film forming agent(s) and plasticizer(s) to achieve a Tg lower than normal human body temperature.

Examples of acceptable classes of film forming agents include acrylic polymers, acrylate copolymers, vinyl pyrrolidone (VP) containing homopolymers and copolymers, polyurethanes, polyolefins and mixtures thereof.

Acrylic Polymers

Acceptable acrylic polymer film forming agents are known in the art and include, but are not limited to, those disclosed in U.S. patent application 2004/0170586 and U.S. patent application 2011/0020263, the entire contents of which are hereby incorporated by reference in their entirety.

"Acrylic polymer film formers" as used herein refers to polymers that are film forming agents and which are based upon one or more (meth)acrylic acid (and corresponding (meth)acrylate) monomers or similar monomers. In further embodiments, the acrylic polymer film formers do not contain a silicone or siloxane group.

Non-limiting representative examples of such film forming agents include copolymers containing at least one apolar monomer, at least one olefinically unsaturated monomer, and at least one vinylically functionalized monomer.

For the apolar monomers, acrylic monomers which comprise acrylic and methacrylic esters with alkyl groups composed of 4 to 14 C atoms, preferably 4 to 9 C atoms are preferred. Examples of monomers of this kind are n-butyl acrylate, n-butyl methacrylate, n-pentyl acrylate, n-pentyl methacrylate, n-amyl acrylate, n-hexyl acrylate, hexyl methacrylate, n-heptyl acrylate, n-octyl acrylate, n-octyl methacrylate, n-nonyl acrylate, isobutyl acrylate, isooctyl acrylate, isooctyl methacrylate, and their branched isomers, such as, for example, 2-ethylhexyl acrylate, 2-ethylhexyl methacrylate.

For olefinically unsaturated monomers, it is preferred to use monomers having functional groups selected from hydroxyl, carboxyl, sulphonic acid groups, phosphonic acid groups, acid anhydrides, epoxides, and amines. Particularly preferred examples of olefinically unsaturated monomers include acrylic acid, methacrylic acid, itaconic acid, maleic acid, fumaric acid, crotonic acid, aconitic acid, dimethylacrylic acid, beta-acryloyloxypropionic acid, trichloracrylic acid, vinylacetic acid, vinylphosphonic acid, itaconic acid, maleic anhydride, hydroxyethyl acrylate, hydroxypropyl acrylate, hydroxyethyl methacrylate, hydroxypropyl methacrylate, 6-hydroxyhexyl methacrylate, allyl alcohol, glycidyl acrylate, glycidyl methacrylate.

For vinylically functionalized compounds, preferred monomers include monomers which are copolymerizable with one or both of the previously discussed monomers and include, for example, methyl acrylate, ethyl acrylate, propyl acrylate, methyl methacrylate, ethyl methacrylate, benzyl acrylate, benzyl methacrylate, sec-butyl acrylate, tert-butyl acrylate, phenyl acrylate, phenyl methacrylate, isobornyl acrylate, isobornyl methacrylate, tert-butylphenyl acrylate, tert-butylphenyl methacrylate, dodecyl methacrylate, isodecyl acrylate, lauryl acrylate, n-undecyl acrylate, stearyl acrylate, tridecyl acrylate, behenyl acrylate, cyclohexyl methacrylate, cyclopentyl methacrylate, phenoxyethyl acrylate, phenoxyethyl methacrylate, 2-butoxyethyl methacrylate, 2-butoxyethyl acrylate, 3,3,5-trimethylcyclohexyl acrylate, 3,5-dimethyladamantyl acrylate, 4-cumylphenyl methacrylate, cyanoethyl acrylate, cyanoethyl methacrylate, 4-biphenyl acrylate, 4-biphenyl methacrylate, 2-naphthyl acrylate, 2-naphthyl methacrylate, tetrahydrofurfuryl acrylate, diethylaminoethyl acrylate, diethylaminoethyl methacrylate, dimethylaminoethyl acrylate, dimethylaminoethyl methacrylate, 2-butoxyethyl acrylate, 2-butoxyethyl methacrylate, methyl 3-methoxyacrylate, 3-methoxybutyl acrylate, phenoxyethyl acrylate, phenoxyethyl methacrylate, 2-phenoxyethyl methacrylate, butyldiglycol methacrylate, ethylene glycol acrylate, ethylene glycol monomethylacrylate, methoxy-polyethylene glycol methacrylate 350, methoxy-polyethylene glycol methacrylate 500, propylene glycol monomethacrylate, butoxydiethylene glycol methacrylate, ethoxytriethylene glycol methacrylate, dimethylaminopropylacrylamide, dimethylaminopropylmethacrylamide, N-(1-methylundecyl)acrylamide, N-(n-butoxymethyl)acrylamide, N-(butoxymethyl) methacrylamide, N-(ethoxymethyl)acrylamide, N-(n-octadecyl)acrylamide, and also N,N-dialkyl-substituted amides, such as, for example, N,N-dimethylacrylamide, N,N-dimethylmethacrylamide, N-benzylacrylamides, N-isopropylacrylamide, N-tert-butylacrylamide, N-tert-octylacrylamide, N-methylolacrylamide, N-methylolmethacrylamide, acrylonitrile, methacrylonitrile, vinyl ethers, such as vinyl methyl ether, ethyl vinyl ether, vinyl isobutyl ether, vinyl esters, such as vinyl acetate, vinyl chloride, vinyl halides, vinylidene chloride, vinylidene halide, vinylpyridine, 4-vinylpyridine, N-vinylphthalimide, N-vinyllactam, N-vinylpyrrolidone, styrene, a- and p-methylstyrene, a-butylstyrene, 4-n-butylstyrene, 4-n-decylstyrene, 3,4-dimethoxystyrene, macromonomers such as 2-polystyrene-ethyl methacrylate (molecular weight Mw of 4000 to 10 g/mol), poly(methyl methacrylate)ethyl methacrylate (Mw of 2000 to 8000 g/mol).

An example of an acrylic polymer is a copolymer of acrylic acid, isobutyl acrylate and isobornyl acetate such as that sold under the names Pseudoblock (Chimex) and Synamer-3. In both of these commercial products, the copolymer is present with a solvent in a 1:1 ratio (50% solid). Another preferred film former is Poly(isobornyl methacrylate-8 co-isobornyl acrylate-co-isobutyl acrylate-co-acrylic acid) at 50% of active material in 50% of octyldodecyl neopentanoate, (Mexomere PAZ from Chimex).

Vinylpyrrolidone Polymers

Acceptable vinylpyrrolidone homopolymers or copolymers include, for example, crosslinked or non-crosslinked vinylpyrrolidone homopolymers such as the Polymer ACP-10, as well as copolymers produced from alpha-olefin and vinylpyrrolidone in which, preferably, the copolymer contains vinylpyrrolidone and an alkyl component containing at least one C4-C30 moiety in a concentration preferably from 10 to 80 percent such as those available from Ashland under the Ganex name such as, for example, VP/eicosene (GANEX V-220) and VP/tricontanyl copolymer (GANEX WP660).

According to preferred embodiments, the film forming agent(s) is/are preferably present in an amount of from about 0.05% to about 90% by weight, preferably from 0.08% to 80% by weight, and preferably from 0.1% to 60% by weight of the total weight of the component in which they are found, including all ranges and subranges therebetween.

According to preferred embodiments, the film forming agent(s) is/are preferably present in an amount of from about 0.1% to 60% by weight, preferably from 0.2% to 55% by weight, and preferably from 0.3% to 50% by weight of the total weight of the composition, including all ranges and subranges therebetween.

High Viscosity Ester

In one or more embodiments, cosmetic composition of the present invention may also contains at least one high viscosity ester. Examples thereof include, but not limited to, $C_1$-$C_{30}$ monoesters and polyesters of sugars and related materials. These esters are derived from a sugar or polyol moiety and one or more carboxylic acid moieties. Depending on the constituent acid and sugar, these esters can be in either liquid or solid form at room temperature. Suitable liquid esters include, but are not limited to: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof. Suitable solid esters may include, but are not limited to: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterifying carboxylic acid moieties are laurate, linoleate and behenate in a 1:3:4 molar ratio. In an embodiment, the ester is a sucrose polyester in which the degree of esterification is 7-8, and in which the fatty acid moieties are C18 mono- and/or di-unsaturated and behenic, in a molar ratio of unsaturates:behenic of 1:7 to 3:5. In another embodiment, the sugar polyester is the octaester of sucrose in which there are about 7 behenic fatty acid moieties and about oleic acid moiety in the molecule. Other materials may include cottonseed oil or soybean oil fatty acid esters of sucrose.

In one or more embodiments, the high viscosity ester comprises sucrose acetate isobutyrate. One example of a suitable sucrose acetate isobutyrate compound is SAIB-100®, commercially available from Eastman®, Kingsport, Tenn. This ester has a viscosity of about 100,000 cps at 30° C. and a refractive index of about 1.5 at 20° C. Acrylic Polymers Acceptable acrylic polymer film forming agents are known in the art and include, but are not limited to, those disclosed in U.S. patent application 2004/0170586 and U.S. patent application 2011/0020263, the entire contents of which are hereby incorporated by reference in their entirety.

Silicone-Containing Film Forming Agent (Film Former)

Compositions of the present invention may comprise at least one silicone-containing film forming agent. As used herein, "silicone-containing film forming agent" refers to a film forming agent that contains silicone. In one or more embodiments, "silicone-containing film forming agent" includes polymers that contain at least about 2.5%, 5%, 10%, 20%, 30%, 40%, 50%, 60%, 70%, 80%, 90%, 95%, or 99% silicone by weight. Silicone-containing film forming agents are known in the art, and any silicone-containing film forming agent may be used. According to preferred embodiments, at least one silicone-containing film forming agent having at least one glass transition temperature lower than 60° C., preferably lower than 55° C., preferably lower than 50° C., and preferably lower than normal human body temperature (98.6° F.), is included in the composition of the present invention. Preferably, the at least one silicone-containing film forming agent has all of its glass transition temperature(s) below 60° C., preferably below than 55° C., preferably below than 50° C., and preferably below than normal human body temperature (98.6° F.). The Tg property of the at least one silicone-containing film forming agent can result from various ways known in the art such as, for example, the Tg of the silicone-containing film forming agent itself, the combination of different film forming agents to achieve a Tg lower than normal human body temperature, or the combination of film forming agent(s) and plasticizer(s) to achieve a Tg lower than normal human body temperature.

Examples of acceptable classes of silicone-containing film forming agents include silicone resins, silicone acrylate copolymers. vinyl pyrrolidone (VP) containing copolymers, polyurethanes, polyolefins and mixtures thereof.

In one or more embodiments, the silicone-containing film forming agent(s) is/are selected from the group consisting of silicone resins, silicone acrylate copolymers mixtures thereof.

Silicone Resin

As used herein, the term "resin" means a crosslinked or non-crosslinked three-dimensional structure. According to one or more embodiments of the present invention, Component A comprises at least one silicone acrylate. Silicone resin nomenclature is known in the art as "MDTQ" nomenclature, whereby a silicone resin is described according to the various monomeric siloxane units which make up the polymer.

Each letter of "MDTQ" denotes a different type of unit. The letter M denotes the monofunctional unit $(CH_3)_3SiO_{1/2}$. This unit is considered to be monofunctional because the silicone atom only shares on oxygen when the unit is part of a polymer. The "M" unit can be represented by the following structure:

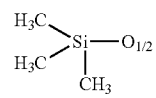

At least one of the methyl groups of the M unit may be replaced by another group, e.g., to give a unit with formula $[R(CH_3)_2]SiO_{1/2}$, as represented in the following structure:

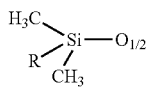

wherein R is chosen from groups other than methyl groups. Non-limiting examples of such groups other than methyl groups include alkyl groups other than methyl groups, alkene groups, alkyne groups, hydroxyl groups, thiol groups, ester groups, acid groups, ether groups, wherein the groups other than methyl groups may be further substituted.

The symbol D denotes the difunctional unit $(CH_3)_2SiO_{2/2}$ wherein two oxygen atoms bonded to the silicone atom are used for binding to the rest of the polymer. The "D" unit, which is the major building block of dimethicone oils, can be represented as:

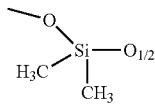

At least one of the methyl groups of the D unit may be replaced by another group, e.g., to give a unit with formula $[R(CH_3)_2]SiO_{1/2}$.

The symbol T denotes the trifunctional unit, $(CH_3)SiO_{3/2}$ and can be represented as:

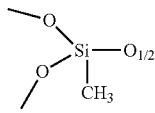

At least one of the methyl groups of the T unit may be replaced by another group, e.g., to give a unit with formula $[R(CH_3)_2]SiO_{1/2}$.

Finally, the letter Q means a tetrafunctional unit $SiO_{4/2}$ in which the silicon atom is bonded to four hydrogen atoms, which are themselves bonded to the rest of the polymer.

Thus, a vast number of different silicone polymers can, be manufactured. Further, it would be clear to one skilled in the art that the properties of each of the potential silicone polymers will vary depending on the type(s) of monomer(s), the type(s) of substitution(s), the size of the polymeric chain, the degree of cross linking, and size of any side chain(s).

Non-limiting examples of silicone polymers include siloxysilicates and silsesquioxanes.

A non-limiting example of a siloxysilicate is trimethylsiloxysilicate, which may be represented by the following formula:

(i.e, MQ units) wherein x and y may, for example, range from 50 to 80. Silsesquioxanes, on the other hand, may be represented by the following formula:

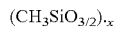

(i.e., T Units) wherein x may, for example, have a value of up to several thousand.

Resin MQ, which is available from Wacker, General Electric and Dow Corning, is an example of an acceptable commercially-available siloxysilicate. For example, trimethylsiloxysilicate (TMS) is commercially available from General Electric under the tradename SR1000 and from Wacker under the tradename TMS 803. TMS is also commercially available from Dow Chemical in a solvent, such as for example, cyclomethicone. However, according to the present invention, TMS may be used in the form of 100% active material, that is, not in a solvent.

Suitable silicon resins comprising at least one T unit in accordance with the present invention are disclosed, for example, in U.S. patent application publication numbers 2007/0166271, 2011/0038820, 2011/0002869, and 2009/0214458, the entire contents of which are hereby incorporated by reference in their entirety.

Where the silicone resin contains at least one T unit, it may thus be, for example, a T, MT, MTQ or MDTQ resin.

According to preferred embodiments, the unit composition of the silicone resin can be at least 50% T units, or at least 70% T units, or at least 80% T units, or at least 90% T units.

In the M, D and T units listed as examples above, at least one of the methyl groups may be substituted. According to preferred embodiments, the at least one silicone resin comprising at least one trifunctional unit of formula $(R)SiO_{3/2}$ is chosen from the silsesquioxanes of formula: $((R')SiO_{3/2})_x$, in which x ranges from 100 to 500 and R' is chosen, independently by trifunctional unit, from a hydrocarbon-based group containing from 1 to 10 carbon atoms or a hydroxyl group, on the condition that at least one R' is a hydrocarbon-based group. According to preferred embodiments, the hydrocarbon-based group containing from 1 to 10 carbon atoms is a methyl group. According to preferred embodiments, the at least one silicone resin comprising at least one trifunctional unit of formula $(R)SiO_{3/2}$ is chosen from the silsesquioxanes of the formula: $((R')SiO_{3/2})_x$, in which x ranges from 100 to 500 and R' is chosen, independently by unit, from $CH_3$, a hydrocarbon-based group containing from 2 to 10 carbon atoms, or a hydroxyl group, on the condition that at least one R' is a hydrocarbon-based group.

According to preferred embodiments, the T resins may contain M, D and Q units such that at least 80 mol % or at least 90 mol %, relative to the total amount of silicones, are T units. The T resins may also contain hydroxyl and/or alkoxy groups. The T resins may have a total weight of hydroxyl functions ranging from 2% to 10% and a total weight of alkoxy functions that may be up to 20%; in some embodiments, the total weight of hydroxyl functions ranges from 4% to 8% and the total weight of alkoxy functions may be up to 10%.

The silicone resin may be chosen from silsesquioxanes that are represented by the following formula: $((CH_3)SiO_{3/2})_x$, in which x may be up to several thousand and the $CH_3$ group may be replaced with an R group, as described previously in the definition of the T units. The number x of T units of the silsesquioxane may be less than or equal to 500, or it may range from 50 to 500, including all ranges and subranges therebetween. The molecular weight of the silicone resin may range from about 500, 1000, 5,000, 10,000, 15,000 or 20,000 g/mol to about 30,000, 35,000, 40,000, 45,000, 50,000, 75,000 or 100,000 g/mol, including all ranges and subranges therebetween.

As suitable examples of these silicone resins containing at least one T unit, mention may be made of:

polysilsesquioxanes of formula $((R)SiO_{3/2})_x$ (T units) in which x is greater than 100, in which the R groups may independently be methyl or other substituents as defined above;

polymethylsilsesquioxanes, which are polysilsesquioxanes in which R is a methyl group. Such polymethylsilsesquioxanes are described, for example, in U.S. Pat. No. 5,246,694, the entire contents of which is hereby incorporated by reference in its entirety;

polypropylsilsesquioxanes, in which R is a propyl group. These compounds and their synthesis are described, for example, in patent application WO 2005/075567, the entire contents of which is hereby incorporated by reference in its entirety; and polyphenylsilsesquioxanes, in which R is a phenyl group. These compounds and their synthesis are described, for example, in patent application US 2004/0180011, the entire contents of which is hereby incorporated by reference in its entirety.

Examples of commercially available polymethylsilsesquioxane resins that may be mentioned include those sold:

by the company Wacker under the reference Resin MK such as Belsil PMS MK: polymer comprising $CH_3SiO_{3/2}$ repeating units (T units), which may also comprise up to 1% by weight of $(CH_3)_2SiO_{2/2}$ units (D units) and having an average molecular weight of about 10 000 g/mol. It is thought that the polymer is in a "cage" and "ladder" configuration as represented in the figures below. The average molecular weight of the units in "cage" configuration has been calculated as 536 g/mol. The majority of the polymer is in the "ladder" configuration with ethoxy groups at the ends. These ethoxy groups represent 4.5% by mass of the polymer. As these end groups can react with water, a small and variable amount of SiOH groups may also be present; and by the company Shin-Etsu under the references KR-220L, which are composed of T units of formula $CH_3SiO_{3/2}$ and have Si—OH (silanol) end groups, under the reference KR-242A, which comprise 98% of T units and 2% of dimethyl D units and have Si—OH end groups or alternatively under the reference KR-251 comprising 88% of T units and 12% of dimethyl D units and have Si—OH end groups.

Examples of commercially available polypropylsilsesquioxane resins that may be mentioned include those sold:

by the company Dow Corning under the reference Dow Corning 670 Fluid or 680 Fluid. Typically such commercially available products are polypropylsilsesquioxane diluted in volatile oil such as volatile hydrocarbon oil or volatile silicone oil such as D5. Dow Corning 670 and 680 Fluids have a general formula of $R_nSiO_{(4-n)/2}$ wherein R is independently chosen from a hydrogen atom and a monovalent hydrocarbon group comprising 3 carbon atoms, wherein more than 80 mole % of R are propyl groups, n is a value from 1.0 to 1.4, more than 60 mole % of the copolymer comprises $RSiO_{3/2}$ units, and having a hydroxyl or alkoxy content from 0.2 to 10% by weight, for example between 1 and 4% by weight, preferably between 5 and 10% by weight, and more preferably between 6 and 8% by weight. Preferably, the polypropylsilsesquioxane resin has a molecular weight from about 5,000, 7,000, 10,000, 15,000, 20,000, 25,000 to about 30,000, 50,000, 75,000, 100,000 g/mol and a Tg of less than about 37° C., from about −100, −50, −37, or −20 to about 37° C.

Examples of commercially available polyphenylsilsesquioxane resins that may be mentioned include those sold:

by the company Dow Corning under the reference Dow Corning 217 Flake Resin, which is a polyphenylsilsesquioxane with silanol end groups; and by the company Wacker under the reference Belsil SPR 45 VP.

Silicone Acrylate Copolymer

Suitable silicone acrylate copolymers include polymers comprising a siloxane group and a hydrocarbon group. In some embodiments, such silicone acrylate copolymers comprise at least about 10%, 20%, 30%, 40%, 50%, 60%, 70%, 80%, or 90% silicone by weight. For example, suitable polymers include polymers comprising a hydrocarbon backbone such as, for example, a backbone chosen from vinyl polymers, methacrylic polymers, and/or acrylic polymers and at least one chain chosen from pendant siloxane groups, and polymers comprising a backbone of siloxane groups and at least one pendant hydrocarbon chain such as, for example, a pendant vinyl, methacrylic and/or acrylic groups.

The at least one silicone acrylate copolymer can be chosen from silicone/(meth)acrylate copolymers, such as those as described in U.S. Pat. Nos. 5,061,481, 5,219,560, and 5,262,087, and U.S. patent application 2012/0301415, the entire contents of all of which are hereby incorporated by reference.

The at least one silicone acrylate copolymer may be selected from polymers derived from non-polar silicone copolymers comprising repeating units of at least one polar (meth)acrylate unit and vinyl copolymers grafted with at least one non-polar silicone chain. Non-limiting examples of such copolymers are acrylates/dimethicone copolymers such as those commercially available from Shin-Etsu, for example, the products sold under the tradenames KP-545 (cyclopentasiloxane (and) acrylates/dimethicone copolymer), KP-543 (butyl acetate (and) acrylates/dimethicone copolymer), KP-549 (methyl trimethicone (and) acrylates/dimethicone copolymer), KP-550 (INCI name: isododecane (and) acrylate/dimethicone copolymer), KP-561 (acrylates/stearyl acrylate/dimethicone acrylates copolymer), KP-562 (acrylates/behenyl acrylate/dimethicone acrylates copolymer), and mixtures thereof. Additional examples include the acrylate/dimethicone copolymers sold by Dow Corning under the tradenames FA 4001 CM SILICONE ACRYLATE (cyclopentasiloxane (and) acrylates/polytrimethylsiloxymethacrylate copolymer) and FA 4002 ID SILICONE ACRYLATE (isododecane (and) acrylates/polytrimethylsiloxymethacrylate Copolymer), and mixtures thereof.

Further non-limiting examples of such polymers and their synthesis are disclosed, for example, in U.S. Pat. Nos. 4,972,037, 5,061,481, 5,209,924, 5,849,275, and 6,033,650, and PCT applications WO 93/23446, WO 95/06078 and WO 01/32737, the disclosures of all of which are hereby incorporated by reference. These polymers may be sourced from various companies. One such company is Minnesota Mining and Manufacturing Company which offers these types of polymers under the tradenames "Silicone Plus" polymers (for example, poly(isobutyl methacrylate-co-methyl FOSEA)-g-poly(dimethylsiloxane), sold under the tradename SA 70-5 IBMMF).

Other non-limiting examples of useful silicone acrylate copolymers include silicone/acrylate graft terpolymers, for example, the copolymers described in PCT application WO 01/32727, the disclosure of which is hereby incorporated by reference.

Other useful polymers include those described in U.S. Pat. No. 5,468,477, the disclosure of which is hereby incorporated by reference. A non-limiting example of these polymers is poly(dimethylsiloxane)-g-poly(isobutyl methacrylate), which is commercially available from 3M Company under the tradename VS 70 IBM.

Suitable silicone acrylate copolymers include silicone/(meth)acrylate copolymers, such as those as described in U.S. Pat. Nos. 5,061,481, 5,219,560, and 5,262,087, the disclosures of which are hereby incorporated by reference. Still further non-limiting examples of silicone film formers are non-polar silicone copolymers comprising repeating units of at least one polar (meth)acrylate unit and vinyl copolymers grafted with at least one non-polar silicone chain. Non-limiting examples of such copolymers are acrylates/dimethicone copolymers such as those commercially available from Shin-Etsu, for example, the product sold under the tradename KP-545, or Other non-limiting examples of silicone film formers suitable for use in the present invention are silicone esters comprising units of formulae (A) and (B), disclosed in U.S. Pat. Nos. 6,045,782, 5,334,737, and 4,725,658, the disclosures of which are hereby incorporated by reference:

$$R_a R^E_b SiO_{[4-(a+b)/2]} \quad \text{(A); and}$$

$$R'_x R^E_y SiO_{1/2} \quad \text{(B)}$$

wherein

R and R', which may be identical or different, are each chosen from optionally substituted hydrocarbon groups;

a and b, which may be identical or different, are each a number ranging from 0 to 3, with the proviso that the sum of a and b is a number ranging from 1 to 3, x and y, which may be identical or different, are each a number ranging from 0 to 3, with the proviso that the sum of x and y is a number ranging from 1 to 3;

$R_E$, which may be identical or different, are each chosen from groups comprising at least one carboxylic ester.

According to preferred embodiments, $R^E$ groups are chosen from groups comprising at least one ester group formed from the reaction of at least one acid and at least one alcohol. According to preferred embodiments, the at least one acid comprises at least two carbon atoms. According to preferred embodiments, the at least one alcohol comprises at least ten carbon atoms. Non-limiting examples of the at least one acid include branched acids such as isostearic acid, and linear acids such as behenic acid. Non-limiting examples of the at least one alcohol include monohydric alcohols and polyhydric alcohols, such as n-propanol and branched etheralkanols such as (3,3,3-trimethylolpropoxy)propane.

Further non-limiting examples of the at least one silicone acrylate copolymer film former include liquid siloxy silicates and silicone esters such as those disclosed in U.S. Pat. No. 5,334,737, the disclosure of which is hereby incorporated by reference, such as diisostearoyl trimethylolpropane siloxysilicate and dilauroyl trimethylolpropane siloxy silicate, which are commercially available from General Electric under the tradenames SF 1318 and SF 1312, respectively.

According to one or more embodiments of the present invention, Component A comprises at least one silicone acrylate and at least one silicone resin. Preferably, the at least one silicone resin is a polypropylsilsesquioxane resin.

According to preferred embodiments, the film forming agent(s) is/are preferably present in an amount of from about 0.01%, 0.05%, 0.08%, 1%, 2%, 3%, 4%, 5%, 6%, 7%, 8%, 9%, 10%, 11%, 12%, 13%, 14%, 15%, 20%, 25%, 30%, 35% to about 20%, 25%, 30%, 35%, 40%, 50%, 60%, 70%, 80% or 90%. In one or more embodiments, these amounts pertain to the amount of silicone-containing film forming agent. In some embodiments, these amounts pertain to the total amount of film forming agents if there are others present besides the at least one silicone-containing film forming agent. In further embodiments, the film forming agent(s) is/are preferably present in an amount of from about 0.01% to about 90% by weight, preferably from 0.08% to 80% by weight, and preferably from 0.1% to 60% by weight of the total weight of the component in which they are found, including all ranges and subranges therebetween.

According to preferred embodiments, the film forming agent(s) is/are preferably present in an amount of from about 0.1% to 60% by weight, preferably from 0.2% to 55% by weight, and preferably from 0.3% to 50% by weight of the total weight of the composition, including all ranges and subranges therebetween.

Silicone Compounds

In one or more embodiments, Component B comprises one or more silicone compounds. As used herein, "silicone compound" refers to a compound comprising silicone having a surface energy lower than that of the silicone-containing film forming agents in Component A. In one or more embodiments, the term refers to a compound, which may be polymeric, comprising a silicon bonded to a minimum of one oxygen, and in even further embodiments, two oxygens. In some embodiments, the silicon is bonded to a hydrocarbon (e.g., C1-22 linear, branched, and/or aryl). In further embodiments, the hydrocarbon is selected from the group consisting of methyl, ethyl, propyl, and phenyl. In one or more embodiments, the silicone compound comprises a polydimethylsiloxane (PDMS). In some embodiments, the silicone compound itself may be linear, branched or dendritic. In further embodiments, the silicone compound is linear or substantially linear. In one or more embodiments, the silicone compound comprises a chain termination selected from the group consisting of hydrocarbon, alcohol, ester, acid, ketone, amine, amide, epoxy, vinylogous (e.g. alkene or alkyne group), halogen, hydride, and the like. For example, in embodiments where the silicone compound comprises polydimethylsiloxane, the compound may be chain end terminated with an —OH or a methyl group.

In one or more embodiments, the term "silicone compound" includes, but is not limited to, silicone gums, silicone fluids, silicone wax, and the like. The silicone compounds may impart properties on the composition (e.g., enhance shine or matte quality). In one or more embodiments, the silicone compounds are present in an amount sufficient to achieve a viscosity of greater than about 1,000 cSt and/or less than about 22,000,000 cSt. In some embodiments, the viscosity ranges from about 1,000, 5,000, 10,000, 20,000, 30,000, 40,000, 50,000 or 60,000 cSt to about 100,000, 200,000, 300,000, 400,000, 500,000, 600,000, 700,000, 800,000, 900,000, 1,000,000, 5,000,000, 10,000,000 or 22,000,000 cSt.

Shine/Luminosity Enhancing Agents

According to preferred embodiments of the present invention, at least one shine enhancing agent can be added to Component A, Component B, or both. Such shine enhancing agents may impart a luminous and/or dewy effect to compositions described herein, which may be advantageous in the case of foundation compositions. For example, one trend for foundation a dewy/radiant foundation (particularly long-lasting radiance), rather than a fully matte appearance. This is usually achieved through the addition of oils or pearls to the formula, but such formulas may not be long-lasting. The compositions described herein may result in both a dewy/radiant appearance that is also long-lasting. Preferably, the shine enhancing agent is selected from the group consisting of agents, which facilitate self-leveling of a layer, agents which have a high refractive index, or mixtures thereof.

Suitable shine enhancing agents include those compounds having a refractive index ranging from about 1.45 to about 1.60, and a weight average molecular weight of less than 15,000, preferably less than 10,000, and preferably less than 2,000. Examples of such agents include, but are not limited to, phenylated silicones such as those commercialized under the trade name "ABIL AV 8853" by Goldschmidt, those commercialized under the trade names "DC 554", "DC 555", "DC 556" and "SF 558" by Dow Corning, and those commercialized under the trade name "SILBIONE 70633 V 30" by Rhone-Poulenc.

Additional examples of suitable phenylated silicones include, but are not limited to, those commercialized by Wacker Silicones such as BELSIL PDM 20, a phenylated silicone with a viscosity at 25° C. of approximately 20 cSt; BELSIL PDM 200, a phenylated silicone with a viscosity at 25° C. of approximately 200 cSt; BELSIL PDM 1000, a phenylated silicone with a viscosity at 25° C. of approximately 1000 cSt.

Additional examples of suitable shine enhancing agents include, but are not limited to, polycyclopentadiene, poly (propylene glycol) dibenzoate (nD=1.5345), aminopropyl phenyl trimethicone (nD=1.49-1.51), pentaerythrityl tetraoleate commercially available as PURESYN 4E68 (nD=1.473) from ExxonMobil, and PPG-3 benzyl ether myristate commercially available as CRODAMOL STS (nD=1.4696) from Croda Inc.

Particularly preferred shine enhancing agents are the phenylated silicones such as phenyl trimethicone, and trimethyl pentaphenyl trisiloxane, and esters such as pentaerythrityl tetraoleate, and PPG-3 benzyl ether myristate.

Suitable shine enhancing agents include those which provide self-leveling properties to the compositions of the present invention. Suitable examples of such compositions include, but are not limited to, the silicone gums discussed below.

The silicone gum can correspond to the formula:

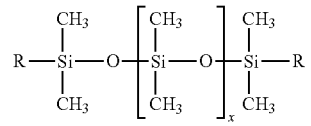

in which:

$R_7$, $R_8$, $R_{11}$ and $R_{12}$ are identical or different, and each is chosen from alkyl radicals comprising from 1 to 6 carbon atoms, $R_9$ and $R_{10}$ are identical or different, and each is chosen from alkyl radicals comprising from 1 to 6 carbon atoms and aryl radicals, X is chosen from alkyl radicals comprising from 1 to 6 carbon atoms, a hydroxyl radical and a vinyl radical, n and p are chosen so as to give the silicone gum a viscosity of from 350 cSt to 50,000,000 cSt, preferably from 500 cSt to 40,000,000 cSt, preferably from 750 cSt to 30,000,000 cSt, preferably from 850 cSt to 20,000,000 cSt, preferably from 950 cSt to 18,000,000 cSt and preferably from 1000 cSt to 10,000,000 cSt, including all ranges and subranges therebetween. A particularly preferred range is from 20,000 cSt to 800,000 cSt, with 25,000 cSt to 750,000 cSt being most preferred.

In general, n and p can each take values ranging from 0 to 10,000, such as from 0 to 5,000.

Among the silicone gums which can be used according to the invention, mention may be made of those for which:

the substituents $R_7$ to $R_{12}$ and X represent a methyl group, p=0 and n=2 700, such as the product sold or made under the name SE30 by the company General Electric, the substituents $R_7$ to $R_{12}$ and X represent a methyl group, p=0 and n=2 300, such as the product sold or made under the name AK 500 000 by the company Wacker, the substituents $R_7$ to $R_{12}$ represent a methyl group, the substituent X represents a hydroxyl group, p=0 and n=2 700, as a 13% solution in cyclopentasiloxane, such as the product sold or made under the name Q2-1401 by the company Dow Corning, the substituents to $R_{12}$ represent a methyl group, the substituent X represents a hydroxyl group, p=0 and n=2 700, as a 13% solution in polydimethylsiloxane, such as the product sold or made under the name Q2-1403 by the company Dow Corning, and the substituents $R_7$, $R_8$, $R_{11}$, $R_{12}$ and X represent a methyl group and the substituents $R_9$ and $R_{10}$ represent an aryl group, such that the molecular weight of the gum is about 600 000, for instance the product sold or made under the name 761 by the company Rhone-Poulenc (Rhodia Chimie).

In preferred embodiments, the silicone gum correspond to the following formula:

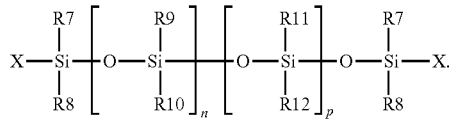

In this formula the terminal Si's can also be other than methyl and may be represented with substitutions on the repeating Si such that the R group is an alkyl of 1 to 6 carbon atoms, which may be linear, branched and/or functionalized selected from methyl, ethyl, propyl, isopropyl, butyl, isobutyl, t-butyl, amyl, hexyl, vinyl, allyl, cycohexyl, phenyl, and mixtures thereof. The silicone gums employed in the present invention may be terminated by triorganosilyl groups of the formula $R'_3$ where R' is a radical of monovalent hydrocarbons containing from 1 to 6 carbon atoms, hydroxyl groups, alkoxyl groups and mixtures thereof.

According to preferred embodiments, Component B/Layer B comprises at least one shine (gloss) enhancing agent.

According to preferred embodiments, Component B/Layer B has a self-leveling property which results in a flatter interface between Layer A and Layer B and/or between Layer B and air, and this flatter interface results in light diffraction, refraction and/or reflection properties for Layer B which enhances the shine of the composition.

According to preferred embodiments of the present invention, at least two silicone compounds such as silicone fluids (for example, phenylated silicones described above) and/or silicone gums are present in the compositions of the present invention.

According to preferred embodiments, if present, agent(s) which facilitate self-leveling of a layer such as silicone gum(s) is/are preferably present in an amount of from about 0.01% to about 90% by weight, preferably from 1% to 85% by weight, and preferably from 5% to 80% by weight of the total weight of the composition, including all ranges and subranges therebetween.

According to preferred embodiments, if present, agent(s) which have a high refractive index such as phenylated silicone oil(s) is/are preferably present in an amount of from about 0.05% to about 90% by weight, preferably from 0.1% to 75% by weight, and preferably from 1% to 50% by weight of the total weight of the composition, including all ranges and subranges therebetween.

According to preferred embodiments of the present invention, at least two silicone compounds such as silicone fluids (for example, phenylated silicones described above) and/or silicone gums are present in the compositions of the present invention.

According to preferred embodiments, the shine enhancing (s) is/are preferably present in an amount of from about 0.05% to about 90% by weight, preferably from 0.1% to 50% by weight, and preferably from 1% to 35% by weight of the total weight of the composition, including all ranges and subranges therebetween.

Matte Enhancing Agents (Mattifyinq Agent)

According to preferred embodiments of the present invention, at least one matte enhancing agent can be added to Component A, Component B, or both. With respect to Component B, the at least one matte enhancing agent can be added regardless of whether Component B is not self-leveling and/or Layer B has refractive properties to impart matte properties to the composition as described above.

Suitable matte enhancing agents include, but are not limited to, mattifying fillers such as, for example, talc, silica, silicone elastomers, and polyamides, and waxes such as, for example, beeswax and copernicia cerifera (camauba) wax.

According to preferred embodiments, the matte enhancing (s) is/are preferably present in an amount of from about 0.05% to about 90% by weight, preferably from 0.1% to 50% by weight, and preferably from 1% to 35% by weight of the total weight of the composition, including all ranges and subranges therebetween.

Soft Focus Agents

According to one or more embodiments, the compositions described herein comprise a soft focus agent. As used herein, the term "soft focus" means that the visual appearance of the skin is more homogenous and matte, leading to the blurring or hiding of skin imperfections.

In some embodiments, the at least soft focus agent may be chosen from hydrophobic silica aerogel particles. Silica aerogels are porous materials obtained by replacing (by drying) the liquid component of a silica gel with air.

Hydrophobic silica aerogel particles useful according to embodiments of the disclosure include silylated silica (INCI name: silica silylate) aerogel particles. The preparation of hydrophobic silica aerogel particles that have been surface-modified by silylation is described more fully in U.S. Pat. No. 7,470,725, incorporated by reference herein. [0068] In various embodiments, aerogel particles of hydrophobic silica surface-modified with trimethylsilyl groups may be chosen. For example, the aerogel sold under the name VM-2260® by the company Dow Corning, the particles of which have an average size of about 1000 microns and a specific surface area per unit of mass ranging from 600 to 800 m2/g, or the aerogel sold under the name VM-2270®, also by the company Dow Corning, the particles of which have an average size ranging from 5 to 15 microns and a specific surface area per unit of mass ranging from 600 to 800 m2/g, may be chosen. In other embodiments, the aerogels sold by the company Cabot under the names Aerogel TLD 201®, Aerogel OGD 201®, and Aerogel TLD 203®, CAB-O-SIL TS-530, CAB-O-SIL TS-610, CAB-O-SIL TS-720, Enova Aerogel MT 1 100®, and Enova Aerogel MT 1200®, may be chosen.

Other soft-focus effect agents can be found in WO/2016100690, the entire contents of which are herein incorporated by reference.

Coloring Agents

According to one or more embodiments of the present invention, compositions further comprising at least one coloring agent are provided. Preferably, such colored compositions can be cosmetic compositions such as, for example, foundations or eye shadows. According to such embodiments, the at least one coloring agent may be chosen from pigments, dyes, nacreous pigments, and pearling agents.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

Representative examples of inorganic pigments useful in the present invention include those selected from the group consisting of rutile or anatase titanium dioxide, coded in the Color Index under the reference CI 77,891; black, yellow, red and brown iron oxides, coded under references CI 77,499, 77, 492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

Representative examples of organic pigments and lakes useful in the present invention include, but are not limited to, D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on cochineal carmine (CI 75,570) and mixtures thereof.

Representative examples of pearlescent pigments useful in the present invention include those selected from the group consisting of the white pearlescent pigments such as mica coated with titanium oxide, mica coated with titanium dioxide, bismuth oxychloride, titanium oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, be present in the composition in a concentration ranging up to 50% by weight of the total weight of the composition, such as from 0.1% to 20%, preferably from 0.1% to 15%, including all ranges and subranges therebetween.

If present, the coloring agents may be present in the composition in a concentration ranging up to 50% by weight of the total weight of the composition, such as from 0.01% to 40%, and further such as from 0.1% to 30%, including all ranges and subranges therebetween. In the case of certain products, the pigments, including nacreous pigments, may, for example, represent up to 50% by weight of the composition.

Embodiments without coloring agents (e.g., an inorganic or organic pigment or pearlizing agents) or with relatively low amounts of coloring agents may be suitable as primers for the skin. As used herein, a "primer" or "undercoat" is a preparatory coating put on materials (e.g., the skin), before the application of subsequent cosmetic product layers. Priming can allow for better adhesion of these subsequent layers to the surface and increase their durability. Priming the skin can also provide additional protection for the material especially in terms of extending the wear. Priming the skin can also help to preserve the integrity of the subsequent cosmetic layers from fading, creasing, continued color intensity throughout the wear, particularly those comprising the compositions disclosed herein. Additionally, the primer can provide a uniform undercoat oftentimes resulting in increased uniformity of the color and texture of the following coat(s). Thus, such primers may act as a base for another foundation or eye shadow composition, which may increase smoothness or help the other composition to better adhere. Such primers may also comprise mattifying agents or elastomers (e.g., silicone elastomers).

Oil Phase

According to preferred embodiments of the present invention, compositions further comprising at least one fatty substance are, provided. Suitable fatty substances include oil(s) and/or wax(es). "Oil" means any non-aqueous medium which is liquid at ambient temperature (25° C.) and atmospheric pressure (760 mm Hg). A "wax" for the purposes of the present disclosure is a lipophilic fatty compound that is solid at ambient temperature (25° C.) and changes from the solid to the liquid state reversibly, having a melting temperature of more than 30° C. and, for example, more than 45° C., which can be as high as 150° C., a hardness of more than 0.5 MPa at ambient temperature, and an anisotropic crystalline organization in the solid state. By taking the wax to its melting temperature, it is possible to use wax(es) by themselves as carriers and/or it is possible to make wax(es) miscible with the oils to form a microscopically homogeneous mixture.

Suitable oils include volatile and/or non-volatile oils. Such oils can be any acceptable oil including but not limited to silicone oils and/or hydrocarbon oils.

According to certain embodiments, the compositions of the present invention preferably comprise one or more volatile silicone oils. Examples of such volatile silicone oils include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
|---|---|---|
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |

Further, a volatile linear silicone oil may be employed in the present invention. Suitable volatile linear silicone oils include those described in U.S. Pat. No. 6,338,839 and WO03/042221, the contents of which are incorporated herein by reference. In one embodiment the volatile linear silicone oil is decamethyltetrasiloxane. In another embodiment, the decamethyltetrasiloxane is further combined with another solvent that is more volatile than decamethyltetrasiloxane.

According to certain embodiments of the present invention, the composition of preferably comprises one or more non-silicone volatile oils and may be selected from volatile hydrocarbon oils, volatile esters and volatile ethers. Examples of such volatile non-silicone oils include, but are not limited to, volatile hydrocarbon oils having from 8 to 16 carbon atoms and their mixtures and in particular branched $C_6$ to $C_{16}$ alkanes such as $C_8$ to $C_{16}$ isoalkanes (also known as isoparaffins), isohexacecane, isododecane, isodecane, and for example, the oils sold under the trade names of Isopar or Permethyl. Preferably, the volatile non-silicone oils have a flash point of at least 40° C.

Non-limiting examples of volatile non-silicone volatile oils are given in Table 2 below.

TABLE 2

| Compound | Flash Point (° C.) |
|---|---|
| Isododecane | 43 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

The volatility of the solvents/oils can be determined using the evaporation speed as set forth in U.S. Pat. No. 6,338,839, the contents of which are incorporated by reference herein.

According to certain embodiments of the present invention, the composition comprises at least one non-volatile oil. Examples of non-volatile oils that may be used in the present invention include, but are not limited to, polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, with $R_6+R_7$ 10, such as, for example, Purcellin oil (cetostearyl octanoate), isononyl isononanoate, octyldodecyl neopentanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms;

$C_8$ to $C_{26}$ fatty alcohols, for instance oleyl alcohol, cetyl alcohol, stearyl alcohol, and cetearly alcohol; and mixtures thereof.

Further, examples of non-volatile oils that may be used in the present invention include, but are not limited to, non-polar oils such as branched and unbranched hydrocarbons and hydrocarbon waxes including polyolefins, in particular Vaseline (petrolatum), paraffin oil, squalene, squalene, hydrogenated polyisobutene, hydrogenated polydecene, polybutene, mineral oil, pentahydrosqualene, and mixtures thereof.

According to preferred embodiments, if present, the at least one oil is present in the compositions of the present invention in an amount ranging from about 5 to about 60% by weight, more preferably from about 10 to about 50% by weight, and most preferably from about 15 to about 35% by weight, based on the total weight of the composition, including all ranges and subranges within these ranges.

According to preferred embodiments of the present invention, the compositions of the present invention further comprise at least one wax. Suitable examples of waxes that can be used in accordance with the present disclosure include those generally used in the cosmetics field: they include those of natural origin, such as beeswax, carnauba wax, candelilla wax, ouricoury wax, Japan wax, cork fibre wax or sugar cane wax, rice wax, montan wax, paraffin wax, lignite wax or microcrystalline wax, ceresin or ozokerite, and hydrogenated oils such as hydrogenated castor oil or jojoba oil; synthetic waxes such as the polyethylene waxes obtained from the polymerization or copolymerization of ethylene, and Fischer-Tropsch waxes, or else esters of fatty acids, such as octacosanyl stearate, glycerides which are concrete at 30° C., for example at 45° C.

According to particularly preferred embodiments of the present invention, the compositions of the present invention further include at least one silicone wax. Examples of suitable silicone waxes include, but are not limited to, silicone waxes such as alkyl- or alkoxydimethicones having an alkyl or alkoxy chain ranging from 10 to 45 carbon atoms, poly(di)methylsiloxane esters which are solid at 30° C. and whose ester chain comprising at least 10 carbon atoms, di(1,1,1-trimethylolpropane) tetrastearate, which is sold or manufactured by Heterene under the name HEST 2T-4S; alkylated silicone acrylate copolymer waxes comprising at least 40 mole % of siloxy units having the formula $(R_2R'SiO_{1/2})_x(R''SiO_{3/2})_y$, where x and y have a value of 0.05 to 0.95, R is an alkyl group having from 1 to 8 carbon atoms, an aryl group, a carbinol group, or an amino group, R is a monovalent hydrocarbon having 9-40 carbon atoms, R" is a monovalent hydrocarbon group having 1 to 8 carbon atoms, an aryl group such as those disclosed in U.S. patent application 2007/0149703, the entire contents of which is hereby incorporated by reference, with a particular example being C30-C45 alkyldimethylsilyl polypropylsilsesquioxane; and mixtures thereof.

According to preferred embodiments of the present invention, the compositions of the present invention further include at least one long-chain alcohol wax. Preferably, the at least one long-chain alcohol wax has an average carbon chain length of between about 20 and about 60 carbon atoms, most preferably between about 30 and about 50 carbon atoms. Suitable examples of long-chain alcohol waxes include but are not limited to alcohol waxes commercially available from Baker Hughes under the Performacol trade name such as, for example, Performacol 350, 425 and 550. Most preferably, the long-chain alcohol wax has a melting temperature range from about 93° C. to about 105° C.

According to preferred embodiments, the compositions of the present invention contain less than 1% wax.

According to preferred embodiments, the compositions of the present invention contain less than 0.5% wax.

According to preferred embodiments, the compositions of the present invention contain no wax.

If present, the wax or waxes may be present in an amount ranging from 1 to 30% by weight relative to the total weight of the composition, for example from 2 to 20%, and for example from 3 to 10%, including all ranges and subranges therebetween.

Additional Additives

According to preferred embodiments, the compositions of the present invention are skin compositions for application to skin such as foundations, primers, eye shadows, etc. In accordance with these embodiments, the compositions of the present invention can contain ingredients typically found in skin compositions such as, for example, coloring agents, active ingredients, humectants, surfactants and fillers. Further, the compositions can contain water or be anhydrous.

The composition of the invention can thus comprise any additive usually used in the field under consideration. For example, dispersants such as poly(12-hydroxystearic acid), antioxidants, essential oils, sunscreens, preserving agents, fragrances, fillers, neutralizing agents, cosmetic and dermatological active agents such as, for example, emollients, moisturizers, vitamins, essential fatty acids, surfactants, silicone elastomers, thickening agents, gelling agents, particles, pasty compounds, viscosity increasing agents can be added. A non-exhaustive listing of such ingredients can be found in U.S. patent application publication no. 2004/0170586, the entire contents of which is hereby incorporated by reference. Further examples of suitable additional components can be found in the other references which have been incorporated by reference in this application. Still further examples of such additional ingredients may be found in the *International Cosmetic Ingredient Dictionary and Handbook* (9th ed. 2002).

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%) relative to the total weight of the composition and further such as from 0.1% to 50% (if present), including all ranges and subranges therebetween.

In one or more embodiments, the composition of the invention is cosmetically or dermatologically acceptable, i.e., it should contain a non-toxic physiologically acceptable medium and should be able to be applied to the skin of human beings.

In particular, suitable gelling agents for the oil phase include, but are not limited to, lipophilic or hydrophilic clays.

The term "hydrophilic clay" means a clay that is capable of swelling in water; this clay swells in water and forms after hydration a colloidal dispersion. These clays are products that are already well known per se, which are described, for example, in the book "Mineralogie des argiles", S. Caillere, S. Henin, M. Rautureau, $2^{nd}$ edition 1982, Masson, the teaching of which is included herein by way of reference. Clays are silicates containing a cation that may be chosen from calcium, magnesium, aluminum, sodium, potassium and lithium cations, and mixtures thereof. Examples of such products that may be mentioned include clays of the smectite family such as montmorillonites, hectorites, bentonites, beidellites and saponites, and also of the family of vermiculites, stevensite and chlorites. These clays may be of natural or synthetic origin.

Hydrophilic clays that may be mentioned include smectite products such as saponites, hectorites, montmorillonites, bentonites and beidellite. Hydrophilic clays that may be mentioned include synthetic hectorites (also known as laponites), for instance the products sold by the company Laporte under the names Laponite XLG, Laponite RD and Laponite RDS (these products are sodium magnesium silicates and in particular sodium lithium magnesium silicates); bentonites, for instance the product sold under the name Bentone HC by the company Rheox; magnesium aluminum silicates, especially hydrated, for instance the products sold by the Vanderbilt Company under the names Veegum Ultra, Veegum HS and Veegum DGT, or calcium silicates, and especially the product in synthetic form sold by the company under the name Micro-cel C.

The term "lipophilic clay" means a clay that is capable of swelling in a lipophilic medium; this clay swells in the medium and thus forms a colloidal dispersion. Examples of lipophilic clays that may be mentioned include modified clays such as modified magnesium silicate (Bentone Gel VS38 from Rheox), and hectorites modified with a $C_{10}$ to $C_{22}$ fatty-acid ammonium chloride, for instance hectorite modified with distearyldimethylammonium chloride (CTFA name: disteardimonium hectorite) sold under the name Bentone 38 CE by the company Rheox or Bentone 38V® by the company Elementis.

In particular, among the gelling agents that may be used, mention may be made of silica particles. Preferably, the silica particles are fumed silica particles.

Suitable silicas include, but are not limited to, hydrophobic silicas, such as pyrogenic silica optionally with hydrophobic surface treatment whose particle size is less than 1 micron, preferably less than 500 nm, preferably less than 100 nm, preferably from 5 nm to 30 nm, including all ranges and subranges therebetween. It is in fact possible to modify the surface of silica chemically, by a chemical reaction producing a decrease in the number of silanol groups present on the surface of the silica. The silanol groups can notably be replaced with hydrophobic groups: a hydrophobic silica is then obtained. The hydrophobic groups can be:

trimethylsiloxyl groups, which are notably obtained by treatment of pyrogenic silica in the presence of hexamethyldisilazane. Silicas treated in this way are called "Silica silylate" according to the CTFA (6th edition, 1995). They are for example marketed under the references "AEROSIL R812®" by the company Degussa, "CAB-O-SIL TS-530®" by the company Cabot;

dimethylsilyloxyl or polydimethylsiloxane groups, which are notably obtained by treatment of pyrogenic silica in the presence of polydimethylsiloxane or dimethyldichlorosilane. Silicas treated in this way are called "Silica dimethyl silylate" according to the CTFA (6th edition, 1995). They are for example marketed under the references "AEROSIL R972®", "AEROSIL R974®" by the company Degussa, "CAB-O-SIL TS-610®", "CAB-O-SIL TS-720®" by the company Cabot.

In particular, suitable emollients may include, but are not limited to, the following: natural and synthetic oils such as mineral, plant and animal oils; fats and waxes; fatty alcohols and acids, and their esters; esters and ethers of (poly) alkylene glycols; hydrocarbons such as petrolatum and squalane; lanolin alcohol and its derivatives; animal and plant triglycerides; and stearyl alcohol.

Non-limiting examples include, without limitation, esters such as isopropyl palmitate, isopropyl myristate, isononyl isonanoate (such as WICKENOL 151 available from Alzo Inc. of Sayreville, N.J.), C12-C15 alkyl benzoates (such as FINSOLV TN from Innospec Active Chemicals), caprylic/capric triglycerides, pentaerythritol tetraoctanoate, mineral oil, dipropylene glycol dibenzoate, PPG-15 stearyl ether benzoate, PPG-2-Myristyl Ether Propionate, ethyl methicone, diethylhexylcyclohexane, hydrocarbon-based oils of plant origin, such as liquid triglycerides of fatty acids containing from 4 to 10 carbon atoms, for instance heptanoic or octanoic acid triglycerides, sunflower oil, corn oil, soybean oil, marrow oil, grapeseed oil, sesame seed oil, hazelnut oil, apricot oil, macadamia oil, arara oil, coriander oil, castor oil, avocado oil, jojoba oil, shea butter oil, caprylyl glycol; synthetic esters and ethers, especially of fatty acids, for instance, Purcellin oil, 2-octyldodecyl stearate, 2-octyldodecyl erucate, isostearyl isostearate, hydroxylated esters, for instance isostearyl lactate, octyl hydroxystearate, octyldodecyl hydroxystearate, diisostearyl malate or triisocetyl citrate, fatty alcohol heptanoates, octanoates or decanoates, polyol esters, for instance propylene glycol dioctanoate, neopentyl glycol diheptanoate and diethylene glycol diisononanoate, pentaerythritol esters, for instance pentaerythrityl tetraisostearate, isopropyl lauroyl sarcosinate, petroleum jelly, polydecenes, hydrogenated polyisobutene such as Parleam oil, and/or the mixture of n-undecane and of n-tridecane sold under the reference Cetiol UT by the company BASF.

Preferably, the emollient agent(s), if present, is present in the composition of the present invention in amounts of active material generally ranging from about 0.1% to about 20%, preferably from about 0.25% to about 15%, and more preferably from about 0.5% to about 10%, by weight, based on the total weight of the composition, including all ranges and subranges in between.

In the case of skin compositions, the composition may comprise skin active agents. Suitable active agents include, for example, anti-acne agents, antimicrobial agents, anti-inflammatory agents, analgesics, anti-erythemal agents, antiruritic agents, antiedermal agents, antipsoriatic agents, antifungal agents, skin protectants, vitamins, antioxidants, scavengers, antiirritants, antibacterial agents, antiviral agents, antiaging agents, protoprotection agents, hair growth enhancers, hair growth inhibitors, hair removal agents, anti-dandruff agents, anti-seborrheic agents, exfoliating agents, wound healing agents, anti-ectoparacitic agents, sebum modulators, immunomodulators, hormones, botanicals, moisturizers, astringents, cleansers, sensates, antibiotics, anesthetics, steroids, tissue healing substances, tissue regenerating substances, hydroxyalkyl urea, amino acids, peptides, minerals, ceramides, biohyaluronic acids, vitamins, skin lightening agents, self-tanning agents, coenzyme Q10, niacinimide, capcasin, caffeine, and any combination of any of the foregoing.

There are also several optional skin adjuvants that may be included. Examples include pH adjusters, emollients, humectants, conditioning agents, moisturizers, chelating agents, propellants, rheology modifiers and emulsifiers such as gelling agents, colorants, fragrances, odor masking agents, UV stabilizer, preservatives, and any combination of any of the foregoing. Examples of pH adjusters include, but are not limited to, aminomethyl propanol, aminomethylpropane diol, triethanolamine, triethylamine, citric acid, sodium hydroxide, acetic acid, potassium hydroxide, lactic acid, and any combination thereof.

Suitable conditioning agents include, but are not limited to, cyclomethicone; petrolatum; dimethicone; dimethiconol; silicone, such as cyclopentasiloxane and diisostearoyl trimethylolpropane siloxy silicate; sodium hyaluronate; isopropyl palmitate; soybean oil; linoleic acid; PPG-12/saturated methylene diphenyldiisocyanate copolymer; urea; amodimethicone; trideceth-12; cekimonium chloride; diphenyl dimethicone; propylene glycol; glycerin; hydroxyalkyl urea; tocopherol; quaternary amines; and any combination thereof.

Suitable preservatives for skin compositions include, but are not limited to, chlorophenesin, sorbic acid, disodium ethylenedinitrilotetraacetate, phenoxyethanol, methylparaben, ethylparaben, propylparaben, phytic acid, imidazolidinyl urea, sodium dehydroacetate, benzyl alcohol, methylehloroisothiazolinone, methylisothiazolinone, and any combination thereof. The heat-protective composition generally contains from about 0.001% to about 20% by weight of preservatives, based on 100% weight of total heat-protective composition. In another aspect, the composition contains from about 0.1% to about 10% by weight of preservatives, based on 100% weight of total heat-protective composition.

The compositions may also optionally comprise UV filters. UV filters are well known in the art for their use in stopping UV radiation. For example, the UV filter may be one or more organic UV filters and/or one or more inorganic UV filters. Non-limiting examples of UV filters include:
i. Sparingly soluble UV filters (not appreciably soluble in either water or oil) such as Methylene Bis-Benzotriazolyl Tetramethylbutylphenol, Tris-Biphenyl Triazine, Methanone, 1,1'-(1,4-piperazinediyl)bis[1-[2-[4-(diethylamino)-2-hydroxybenzoyl]phen-yl]- and mixtures thereof.
ii. Oil soluble organic UV filters (at least partially soluble in oil or organic solvent), such as Bis-Ethylhexyloxyphenol Methoxyphenyl Triazine, Butyl Methoxydibenzoylmethane (BMBM), Oxybenzone, Sulisobenzone, Diethylhexyl Butamido Triazone (DBT), Drometrizole Trisiloxane, Ethylhexyl Methoxycinnamate (EHMC), Ethylhexyl Salicylate (EHS), Ethylhexyl Triazone (EHT), Homosalate, Isoamyl p-Methoxycinnamate, 4-Methylbenzylidene Camphor, Octocrylene (OCR), Polysilicone-15, and Diethylamino Hydroxy Benzoyl Hexyl Benzoate (DHHB);
iii. Inorganic UV filters such as titanium oxide and zinc oxide, iron oxide, zirconium oxide and cerium oxide; and
iv. Water soluble UV filters such as Phenylbenzimidazole Sulfonic Acid (PBSA), Sulisobenzone-sodium salt, Benzydilene Camphor Sulfonic Acid, Camphor Benzalkonium Methosulfate, Cinoxate, Disodium Phenyl Dibenzylmidazole Tetrasulfonate, Terephthalylidene Dicamphor Sulfonic Acid, PABA, and PEG-25 PABA.

In some instances, the UV filter is one or more of: a para-aminobenzoic acid derivative, a salicylic derivative, a cinnamic derivative, a benzophenone or an aminobenzophenone, an anthranillic derivative, a β,β-diphenylacrylate derivative, a benzylidenecamphor derivative, a phenylbenzimidazole derivative, a benzotriazole derivative, a triazine derivative, a bisresorcinyl triazine, an imidazoline derivative, a benzalmalonate derivative, a 4,4-diarylbutadiene derivative, a benzoxazole derivative, a merocyanine, malonitrile or a malonate diphenyl butadiene derivative, a chalcone, or a mixture thereof.

Suitable UV filters can include broad-spectrum UV filters that protect against both UVA and UVB radiation, or UV filters that protect against UVA or UVB radiation. In some instances, the one or more UV filters may be methylene bis-benzotriazolyl tetramethylphenol, diethylamino hydroxybenzoyl hexyl benzoate, coated or uncoated zinc oxide, ethylhexyl methoxycinnamate, isoamyl methoxycinnamate, homosalate ethyl hexyl salicilate, octocrylene, polysilicone-15, butyl methoxydibenzoylmethane, menthyl anthranilate, and ethylhexyl dimethyl PABA.

Furthermore, combinations of UV filters may be used. For example, the combination of UV filters may be octocrylene, avobenzone (butyl methoxydibenzoylmethane), oxybenzone (benzophenone-3), octisalate (ethylhexyl salicylate), and homosalate, as described in U.S. Pat. No. 9,107,843, which is incorporated herein by reference in its entirety.

Methods

According to preferred embodiments of the present invention, methods of treating, caring for and/or making up keratinous material, such as skin, by applying compositions of the present invention to the keratinous material in an amount sufficient to treat, care for and/or make up the keratinous material are provided. Preferably, "making up" the keratin material includes applying at least one coloring agent to the keratin material in an amount sufficient to provide color to the keratin material.

According to yet other preferred embodiments, methods of enhancing the appearance of keratinous material by applying compositions of the present invention to the keratinous material in an amount sufficient to enhance the appearance of the keratinous material are provided.

According to preferred embodiments of the present invention, methods of applying compositions of the present invention to a keratinous material (for example, skin) comprising mixing or blending the composition so that the immiscible components are temporarily miscible, and applying the composition comprising the temporarily miscible components to the keratinous material are provided. In one or more embodiments, composition may be mixed in a mixing pack or may be mixed by hand. Subsequent to application to the keratinous material, the components separate to form a multilayer structure on the keratinous material.

According to preferred embodiments of the present invention, kits comprising (1) at least one container; (2) at least one applicator; and (3) at least one cosmetic composition capable of forming a multilayer structure after application to a keratinous material, wherein the composition comprises at least two immiscible components prior to application.

In accordance with the preceding preferred embodiments, the compositions of the present invention are applied topically to the desired area of the keratin material in an amount sufficient to treat, care for and/or make up the keratinous material, to cover or hide defects associated with keratinous material, skin imperfections or discolorations, or to enhance the appearance of keratinous material. The compositions may be applied to the desired area as needed, preferably once daily, and then preferably allowed to dry before subjecting to contact such as with clothing or other objects. Preferably, the composition is allowed to dry for about 4 minutes or less, more preferably for about 2 minutes or less.

Also in accordance with the preceding preferred embodiments, compositions are preferably contained in a suitable container for cosmetic compositions. Suitable shapes of such containers include, but are not limited to, any geometric shape such as, for example, square, rectangular, pyramidal, oval, circular, hemispherical, etc. Further, the container may be made of flexible or inflexible material.

Similarly, any applicator suitable for application of cosmetic compositions can be used in accordance with the present invention, with suitable examples of types of applicators including, but not limited to, a brush, stick, pad, roller ball, etc.

Preferably, either (1) the container is capable of mixing or blending the composition of the present invention so that the immiscible components are temporarily miscible; (2) the applicator is capable of mixing or blending the composition of the present invention so that the immiscible components are temporarily miscible; or (3) the container and the applicator working together are capable of mixing or blending the composition of the present invention so that the immiscible components are temporarily miscible in accordance with the preceding preferred embodiments. For example, a flexible container by virtue of its flexibility could create sufficient forces when manipulated to temporarily mix or blend the composition of the present invention so that the immiscible components are temporarily miscible; an applicator by virtue of its design could create sufficient forces when withdrawn from the container to temporarily mix or blend the composition of the present invention so that the immiscible components are temporarily miscible; or (3) an inflexible container and an applicator by virtue of their synergistic design elements could create sufficient forces when the applicator is withdrawn from the container to temporarily mix or blend the composition of the present invention so that the immiscible components are temporarily miscible.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

Example 1—Foundation

Preparation

Foundation examples Inventive 2, Comparative 3 and Comparative 4 were prepared using a high speed mixer. To a high speed mixer cup, all polymers were added. The sample was mixed at 2500-3500 RPM until homogenous. The samples typically were opaque and not clear, and homogeneity was deciphered by the sample smoothness. To the freshly mixed sample, pigments, pigment dispersions, and any other particles were added in addition to the QS solvent. The sample was additionally mixed at 2500-3500 RPM until homogenous. Ingredients are as shown in the table below.

Comparative 1 is a commercially available product. Comparative 1 is considered to be comparative because it does not contain a silicone compound and the silicone resin that is used has a high $T_g$.

Comparative 3 is considered to be comparative because it does not contain any film forming agents (i.e., a Component A).

Comparative 4 is considered to be comparative because it does not contain a silicone compound (i.e., a Component B).

Wear Test

Foundation samples were casted onto Byko-Charts Black Scrub Panels P122-10N (6.50×17.00 inches) using a 3 mil wet drawdown bar. Films were allowed to dry for a minimum of five hours. Samples were then abraded using an automatic drawdown machine (Gardco Automatic Drawdown Machine) equipped with Velcro (¾" white 010 PSA 0172) loop side pieces adhered to the lowest bar. Contact between the Velcro adhered bar and the film interface was made and then the bar was automatically dragged across the sample five times (one direction is considered drag across). Samples were then evaluated for removal of product in which a rating of 1 is minimal removal, 2 is intermediate removal, and 3 is complete removal.

Self-Leveling Test

Samples were evaluated for their dried film properties. Samples were casted onto a Byko-Charts Black Scrub Panels P122-10N (6.50×17.00 inches) using a 3 mil wet drawdown bar at room temperature. Samples were allowed to dry for a minimum of 5 hours. After drying, samples were visually and manually evaluated for phase separation and self-leveling properties. In order to assess the phase separation, films were agitated with a gloved index finger by lightly rubbing one stroke across the sample interface. If samples could be roughened it was documented and they were further assessed for recovery of the film by self-leveling. Samples were allowed to rest for a minimum of a 24 hour period and then visually reassessed for interface quality and if there was any level of recovery. Images were also captured of the samples prior to roughening, at initial roughening, and at 24 hours after roughening. After the 24 hour period, it was documented if the sample showed signs of recovery or not.

| RM Name | Comparative 1 | Inventive 2 | Comparative 3 | Comparative 4 |
|---|---|---|---|---|
| Polypropylsilisequioxane Resin (72% Active in Isododecane) | Silicone Resin Containing Technology | 14.58 | 0 | 14.58 |
| Silicone Acrylate Polymer[1] 40% Active in Isododecane) | | 11.25 | 0 | 11.25 |
| Dimethiconol[2] | | 5 | 5 | 0 |
| Pigment | | 12.02 | 12.02 | 12.02 |
| Isododecane | | QS | QS | QS |
| Total | | 100 | 100 | 100 |
| Film Disrupted | No | Yes | Yes - partly removed | Slightly |
| Self-Leveling Property? | No | Yes | No | Yes |
| Wear test - Abrasion Score | 2 | 1 | 2 | 2 |

[1]= Kp550, Shin Etsu
[2]= 1515 Silicone Gum, Dow Corning

As can be seen from the table above, the only composition to allow film disruption and exhibit self-healing was Inventive 1. Comparative 1 did not allow for film disruption, and thus would not exhibit self-healing. Such film setting means that if disturbed enough, the film may flake, a highly undesirable quality in foundation. Inventive 2 allowed for film disruption, and then leveled to the point where disruption could no longer be detected. Comparative 3 allowed for film disruption, but was also partly removed, again an undesired effect in a foundation. Comparative 4 allowed for slight film disruption, and exhibited some self-leveling, but not to the extent of Inventive 1. Thus, Inventive 1 was the foundation sample to exhibit the greatest degree of self-leveling.

As can also be seen from the table above, only Inventive 2 scored a 1 on the wear test, meaning it was the only composition exhibiting minimal removal. All other comparative samples scored a 2, corresponding to intermediate removal.

These results show the nexus between having both film forming agent and silicone compound and achieving good wear self-healing properties. Inventive 2 and Comparative 3 differ in that Comparative 3 does not have any film forming agents, with isododecane increased to maintain the same levels of pigment and dimethiconol. Similarly, Inventive 2 and Comparative 4 differ in that Comparative 4 does not contain dimethiconol, again with isododecane increased to maintain the same levels of pigment and film forming agents. Thus, Inventive 2 can be directly compared to Comparative 3 to see the effect of removing the film forming agents, and Inventive 2 can be directly compared to Comparative 4 to see the effect of removing the silicone compounds.

Indeed, the results demonstrate that self-healing and good wear are exhibited only when both Components A and B are present (i.e., a synergistic effect). Comparative 3 was partly removed during film disruption, exhibited no self-healing and scored a 2 in the wear test. Comparative 4 was slightly disrupted, exhibited self-healing, and also only scored a 2 in the wear test. Inventive 2 outperformed Comparative 3 and 4 in all respects, thereby showing both components are required, and that they have a synergistic effect compared to composition with only one of Component A or B.

Example 2—Primer

Preparation

Primer examples were prepared using a high speed mixer. To a high speed mixer cup, all polymers were added. The sample was mixed at 2500-3500 RPM until homogeneous. The samples were opaque, not clear and the homogeneity was assessed by the sample smoothness. To the freshly mixed samples, filler particles were added. The sample was again mixed at 2500-3500 RPM until homogeneous.

Comparative 6 is a commercially available product.

Self-Leveling Test

Samples were evaluated for their dried film properties. Samples were casted onto a Byko-Charts Black Scrub Panels P122-10N (6.50×17.00 inches) using a 3 mil wet drawdown bar at room temperature. Samples were allowed to dry for a minimum of 5 hours. After drying, samples were visually and manually evaluated for phase separation and self-leveling properties. In order to assess the phase separation, films were agitated with a gloved index finger by lightly rubbing one stroke across the sample interface. If samples could be roughened it was documented and they were further assessed for recovery of the film by self-leveling. Samples were allowed to rest for a minimum of a 24 hour period and then visually reassessed for interface quality and if there was any level of recovery. Images were also captured of the samples prior to roughening, at initial roughening, and at 24 hours after roughening. After the 24 hour period, it was documented if the sample showed signs of recovery or not.

Bulk Phase Separation Assessment

All samples were visually assessed for homogeneity, phase separation, and any additional visual attributes. These evaluations were conducted after the bulk formula was allowed to rest at room temperature for 24 hours after mixing or agitation. If the bulk appeared phase separated or not, the sample was noted.

Adhesion Assessment

Samples were casted onto a BYK Byko-Charts Black Scrub Panels P122-10N (6.50×17.00 inches) using a 3 mil wet drawdown bar at room temperature. Samples were allowed to dry for a minimum of 24 hours. A sheet of ASTM Cross hatch tape (Permacel 99/PA-28060/51596) was applied onto the film and patted down to ensure contact with the film. Tape was removed at 180 degree angle and visually assessed for removal of product. The product was assessed on a three point scale where a 1 is no removal of product a 2 is partial removal of product and a 3 is complete removal of product.

Visual Assessment of Eye Shadow on Top of Primer

Samples were casted onto a BYK Byko-Charts Black Scrub Panels P122-10N (6.50×17.00 inches) using a 3 mil wet drawdown bar at room temperature. Samples were allowed to dry for a minimum of 24 hours. Following the film setting, an eye shadow was applied on top of the primer sample. The product was visually assessed for color intensity and the color consistency to the bulk product. Color intensity was assessed according a 3 point scale where a 1 is very high intensity a 2 is intermediate intensity and a 3 is low intensity. Color consistency was rated based of color pay off versus the bulk color of the eye shadow where a 1 is very similar to the bulk a 2 is somewhat similar and a 3 is very dissimilar to the bulk.

| Raw Material | Inventive 5 | Comparative 6 |
|---|---|---|
| Polypropylsilisquoxane (72% Active in Isododecane) | 44 | On-Market Technology containing MQ Silicone Resin Technology |
| Dimethiconol[1] | 22 | |
| Isododecane (QS) | 33 | |
| Silica Silylate (Aerogel)[2] | 1 | |
| Total | 100 | |
| Bulk Phase Separation | Yes | NA |
| Film Disrupted? | Yes | Yes (Sample was removed from substrate) |
| Self-Leveling? | Yes | No |
| Adhesion Assessment | 1 | 3 |
| Visual Assessment of Color Intensity | 1 | 2 |
| Visual Assessment of Color Consistency to Bulk | 1 | 2 |

[1] = 1515 Silicone Gum, Dow Corning
[2] = DOW CORNING VM-2270 AEROGEL FINE PARTICLES As seen in the table above, on-market commercially available Comparative 6 did not perform as well as Inventive 5 with respect to adhesion assessment, color intensity or color consistency. Moreover, Inventive 5 exhibited self-leveling properties after disruption while Comparative 6 was partly removed during disruption, and did not self-level over time.

What is claimed is:

1. A cosmetic composition capable of forming a multilayer structure after application to skin,
   wherein the cosmetic composition comprises at least two immiscible components:
   Component A which comprises about 0.01% to 60% by weight with respect to the total weight of the composition of at least one silicone- and/or hydrocarbon-containing film forming agent having at least one glass transition temperature which is lower than normal human body temperature; and
   Component B which comprises about 0.01% to 90% by weight with respect to the total weight of the composition of one or more silicone compounds in amounts sufficient to achieve a viscosity of about 1,000 cSt to 22,000,000 cSt,
   wherein the weight ratio of the silicone- and/or hydrocarbon-containing film forming agent(s) in Component A to silicone compound(s) in Component B is from about 1:50 to 1.5:1, and
   wherein, prior to application to skin, the cosmetic composition is mixed such that Component A and Component B are temporarily miscible upon application to skin and, after application to skin, Component A separates from Component B to form a multilayer structure on skin comprising Layer A corresponding to Component A and Layer B corresponding to Component B.

2. The cosmetic composition of claim 1, wherein the cosmetic composition comprises the at least two immiscible components prior to application.

3. The cosmetic composition of claim 1, further comprising a pigment.

4. The cosmetic composition of claim 3, wherein the pigment is an inorganic pigment.

5. The cosmetic composition of claim 4, wherein the inorganic pigment is selected from the group consisting of iron oxide, titanium oxide, ultramarine blue and combinations thereof.

6. The cosmetic composition of claim 1, further comprising a mattifying agent selected from the group consisting of a talc, silica, silicone elastomer, polyamide, wax, and combinations thereof.

7. The cosmetic composition of claim 1, wherein the cosmetic composition is anhydrous.

8. The cosmetic composition of claim 1, wherein Component A comprises at least one silicone-containing film forming agent having at least one glass transition temperature lower than 60° C.

9. The cosmetic composition of claim 1, further comprising a skin active agent, skin adjuvant, or UV filter.

10. The cosmetic composition of claim 1, wherein the silicone compound comprises at least one polymer selected from the group consisting of a silicone gum, a silicone fluid, and mixtures thereof.

11. The cosmetic composition of claim 1, wherein the at least one silicone- and/or hydrocarbon-containing film forming agent comprises a hydrocarbon-containing film forming agent selected from the group consisting of polysaccharides, high viscosity esters, polybutenes, polyisobutenes, polyhydrogenated butenes, acrylic polymers, acrylate copolymers, vinyl pyrrolidone (VP) containing homopolymers and copolymers, polyurethanes, polyolefins and mixtures thereof.

12. The cosmetic composition of claim 1, wherein the at least one at least one silicone- and/or hydrocarbon-containing film forming agent comprises at least one film forming agent selected from the group consisting of a silicone resin, a silicone acrylate copolymer, and mixtures thereof.

13. A kit comprising: (a) the cosmetic composition according to claim 1; (b) at least one container which contains the cosmetic composition according to claim 1; and (c) at least one applicator.

14. The kit of claim 13, wherein the at least one container is configured to mix Components A and B.

15. A method of applying the cosmetic composition of claim 1 to a keratinous material comprising mixing the cosmetic composition to form a mixed composition in which Component A and Component B are temporarily miscible, and applying the mixed composition to the keratinous material.

16. The method of claim 15, wherein the keratinous material comprises skin.

17. The method of claim 15, wherein the silicone compound comprises at least one polymer selected from the group consisting of a silicone gum, a silicone fluid, and mixtures thereof.

18. The method of claim 15, wherein the at least one silicone- and/or hydrocarbon-containing film forming agent comprises a hydrocarbon-containing film forming agent selected from the group consisting of polysaccharides, high viscosity esters, polybutenes, polyisobutenes, polyhydrogenated butenes, acrylic polymers, acrylate copolymers, vinyl pyrrolidone (VP) containing homopolymers and copolymers, polyurethanes, polyolefins and mixtures thereof.

19. The method of claim 15, wherein the at least one at least one silicone- and/or hydrocarbon-containing film forming agent comprises at least one film forming agent selected from the group consisting of a silicone resin, a silicone acrylate copolymer, and mixtures thereof.

20. The method of claim 15, wherein the composition further comprises a pigment.

* * * * *